United States Patent
Yamanaka et al.

(10) Patent No.: US 8,471,018 B2
(45) Date of Patent: Jun. 25, 2013

(54) PHOTOSENSITIZER AND PHOTOVOLTAIC DEVICE

(75) Inventors: Noriyo Yamanaka, Yokohama (JP);
Masaki Minami, Yokohama (JP);
Tsutomu Nakamura, Yokohama (JP);
Hideki Masuda, Nagoya (JP);
Zhengzhe Jin, Nagoya (JP)

(73) Assignees: JX Nippon Oil & Energy Corporation, Tokyo (JP); Nagoya Institute of Technology, Aichi (JP)

( * ) Notice: Subject to any disclaimer, the term of this patent is extended or adjusted under 35 U.S.C. 154(b) by 246 days.

(21) Appl. No.: 12/934,447

(22) PCT Filed: Mar. 25, 2009

(86) PCT No.: PCT/JP2009/001324
§ 371 (c)(1),
(2), (4) Date: Dec. 15, 2010

(87) PCT Pub. No.: WO2009/119085
PCT Pub. Date: Oct. 1, 2009

(65) Prior Publication Data
US 2011/0108117 A1 May 12, 2011

(30) Foreign Application Priority Data

Mar. 26, 2008 (JP) .................................. 2008-080977
Apr. 25, 2008 (JP) .................................. 2008-115831
Nov. 13, 2008 (JP) .................................. 2008-290990

(51) Int. Cl.
*C07F 15/00* (2006.01)
*H01L 51/00* (2006.01)

(52) U.S. Cl.
USPC .................. 546/2; 313/504; 313/498; 546/10

(58) Field of Classification Search
USPC .................. 546/2, 10; 313/504, 498; 428/690
See application file for complete search history.

(56) References Cited

U.S. PATENT DOCUMENTS

| 7,236,288 | B2 | 6/2007 | Shinohara et al. |
| 7,741,559 | B2 | 6/2010 | Kurihara et al. |
| 2006/0198010 | A1 | 9/2006 | Shinohara et al. |
| 2006/0237059 | A1 | 10/2006 | Kurihara et al. |

FOREIGN PATENT DOCUMENTS

| JP | 11176489 A | 7/1999 |
| JP | 2002100417 A | 4/2002 |
| JP | 2004363096 A | 12/2004 |
| JP | 2006243352 A | 9/2006 |
| WO | 2004102724 A1 | 11/2004 |
| WO | 2007006026 A1 | 1/2007 |

OTHER PUBLICATIONS

Jin, Z. et al.: Triarylamine-functionalized Ruthenium dyes for efficient dye-sensitized solar cells. ChemSusChem, vol. 1, pp. 901-904, 2008.*

International Search Report issued on Jun. 30, 2009 in International Application No. PCT/JP2009/001324.

Brian O'Regan et al., "A low-cost, high-efficiency solar cell based on dye-sensitized colloidal TiO2 films", Nature, vol. 353, pp. 737-740, (1991).

Mohammad K. Nazeeruddin et al., "Engineering of Efficient Panchromatic Sensitizers for Nanocrystalline TiO2-Based Solar Cells", J. Am. Chem. Soc., vol. 123, pp. 1613-1624, (2001).

* cited by examiner

*Primary Examiner* — Charanjit Aulakh
(74) *Attorney, Agent, or Firm* — Panitch Schwarze Belisario & Nadel LLP

(57) ABSTRACT

Disclosed is a novel photosensitizer that can absorb light in a wide visible light region and in the case of a very thin film form, can enhance a light absorption efficiency by virtue of a large light absorption coefficient. The photosensitizer is used for metal oxide semiconductor electrodes and comprises a metal complex represented by a general formula $ML^1L^2X_2$, wherein M is a group 8 transition metal of the periodic table, Xs are each independently a halogen atom, a cyano group, a thiocyanate group, an isothiocyanate group, an isocyanate group, an isocyanide group or a hydroxyl group, or a bidentate ligand in the case where Xs are bonded to one another, $L^1$ and $L^2$ are each a ligand having an aromatic ring, and either $L^1$ or $L^2$ has a functional group having a COOH group or $PO(OH)_2$, and when the photosensitizer is adsorbed on a metal oxide semiconductor electrode via ligands $L^1$ and $L^2$, the difference ΔL between the energy levels of ligands $L^1$ and $L^2$ in their excited states, calculated in accordance with a GAUSSIAN03 quantum chemistry calculation program is 0.25 eV or more.

4 Claims, 2 Drawing Sheets

[Fig. 4

PHOTOSENSITIZER AND PHOTOVOLTAIC DEVICE

CROSS-REFERENCE TO RELATED APPLICATION

This application is a section 371 of International Application No. PCT/JP2009/001324, filed Mar. 25, 2009, which was published in the Japanese language on Oct. 1, 2009 under International Publication No. WO 2009/119085 A1 and the disclosure of which is incorporated herein by reference.

TECHNICAL FIELD

The present invention relates to novel photosensitizers and in particular to those suitably used for dye-sensitized solar cells.

BACKGROUND ART

The dye-sensitized solar cell introduced by Gratzel et al. in 1991 is a wet solar cell with working electrodes formed of a porous titanium oxide film spectral-sensitized with a ruthenium complex and reported to have performances equivalent to those of a silicon solar cell (see Non-Patent Document 1 below). This approach has received attention because of its advantages that it enables the use of an inexpensive oxide semiconductor such as titania without purifying the semiconductor to a high purity and thus can provide an inexpensive dye-sensitized solar cell, which can convert light substantially in the whole wavelength region to electricity because of its broad dye absorptivity. However, the known ruthenium complex dye absorbs the visible light but little the infrared light of a wavelength of 700 nm or longer and thus is low in photoelectric-conversion capacity in the infrared region. Therefore, in order to further enhance the conversion efficiency, a development of dye has been demanded, which can absorb not only the visible light but also the infrared light.

Meanwhile, black dye can absorb light of up to 920 nm but is small in light absorption coefficient and thus needs to increase the amount to be adsorbed on a porous titanium oxide film in order to obtain a higher electric current value. Various approaches have been made to increase the amount to be adsorbed on a porous titanium oxide film. Generally, the amount can be increased by increasing the thickness of the film (see Non-Patent Document 2 below). As the film thickness is increased, the conversion efficiency can not be increased significantly due to the occurrence of reductions in open circuit voltage and FF (fill factor) resulting from an increase in reverse electron transfer and a decrease in the electron density in the film.

There is a report that a solar cell is produced using a complex containing an imidazophenanthroline ligand, which, however, can not obtain a sufficient conversion efficiency (see Patent Document 1 below).

Non-Patent Document 1: "NATURE" (Great Britain), Vol. 353, page 737 by B. O' Regan and M. Gratzel Non-Patent Document 2: "Journal of American Chemical Society" (U.S.A) Vol. 123, page 1613, by M. Gratzel Patent Document 1: WO2007/006026

DISCLOSURE OF INVENTION

Technical Problem

The present invention provides a novel photosensitizer that can absorb light in a wide visible light range and has such a large absorption coefficient that makes the photo absorption efficiency higher even on a thin film.

Solution to Problem

As a result of extensive studies concerning metal complex dyes conducted by the inventors, the present invention was accomplished.

That is, the present invention relates to a photosensitizer for metal oxide semiconductor electrodes, wherein it comprises a metal complex represented by formula (I) below, and when it is adsorbed on a metal oxide semiconductor electrode via ligands $L^1$ and $L^2$, the difference $\Delta L$ between the energy levels of ligands $L^1$ and $L^2$ in their excited states, calculated in accordance with a GAUSSIAN03 quantum chemistry calculation program is 0.25 eV or more:

$$ML^1L^2X_2 \qquad (I)$$

wherein M is a group 8 transition metal of the periodic table, Xs are each independently a halogen atom, a cyano group, a thiocyanate group, an isothiocyanate group, an isocyanate group, an isocyanide group or a hydroxyl group, or a bidentate ligand represented by formula (A) below in the case where Xs are bonded to one another, $L^1$ and $L^2$ are each a ligand having an aromatic ring, and either $L^1$ or $L^2$ has a functional group having a COOH group or $PO(OH)_2$ or a functional group to which a COOH group or $PO(OH)_2$ is bonded via π conjugation:

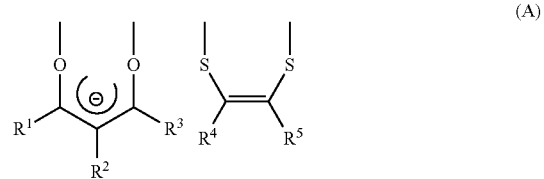

wherein $R^1$ through $R^3$ may be the same or different from each other and are each independently hydrogen, an alkyl group having 1 to 30 carbon atoms, an alkoxyalkyl group having 2 to 30 carbon atoms, a perfluoroalkyl group having 1 to 30 carbon atoms, an aryl group having 6 to 30 carbon atoms, or an aralkyl group having 7 to 30 carbon atoms, and $R^4$ and $R^5$ are each independently hydrogen, a cyano group, an alkyl group having 1 to 20 carbon atoms, a perfluoroalkyl group having 1 to 20 carbon atoms, or an aryl group having 6 to 15 carbon atoms and may be bonded to one another to form a ring.

The present invention also relates to the foregoing photosensitizer wherein in formula (I) $L^1$ is a ligand represented by formula (II) below and $L^2$ is a ligand represented by formula (III) below:

(II)

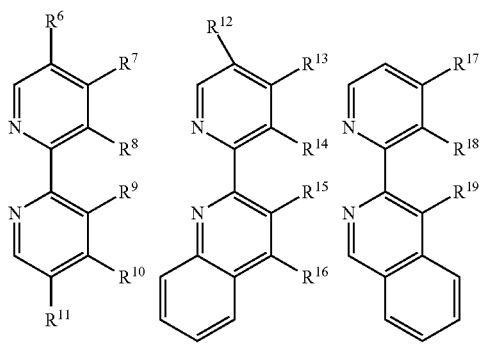
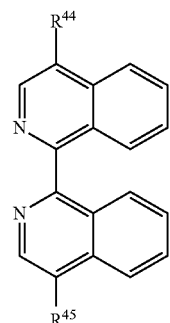

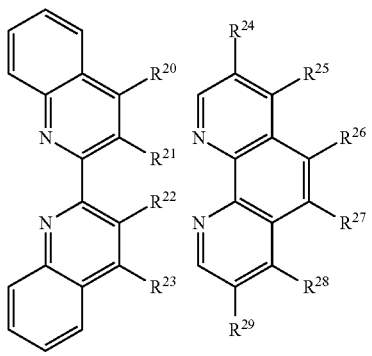

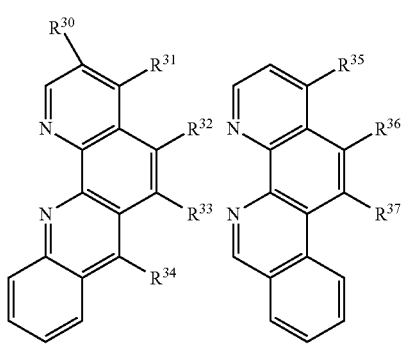

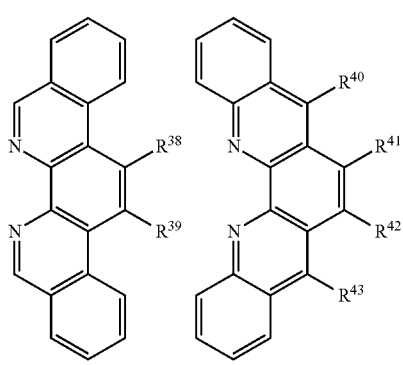

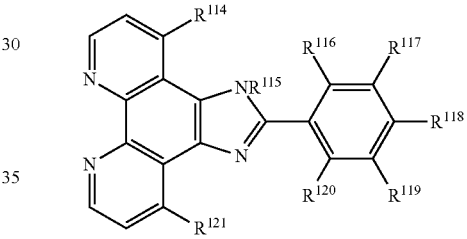

wherein $R^6$ through $R^{11}$, $R^{12}$ through $R^{16}$, $R^{17}$ through $R^{19}$, $R^{20}$ through $R^{23}$, $R^{24}$ through $R^{29}$, $R^{30}$ through $R^{34}$, $R^{35}$ through $R^{37}$, $R^{38}$ through $R^{39}$, $R^{40}$ through $R^{43}$, and $R^{44}$ through $R^{45}$ may be the same or different from each other and are each independently a functional group having a COOH group or $PO(OH)_2$, a functional group to which a COOH group or $PO(OH)_2$ is bonded via π conjugation, hydrogen, an alkyl group having 1 to 30 carbon atoms, an alkenyl group, an aryl group, an alkoxy group, or an amino group;

(III)

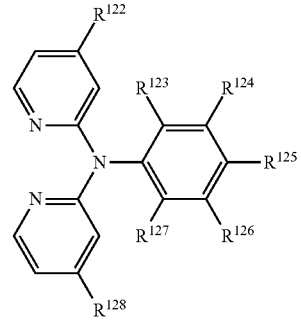

wherein $R^{114}$ through $R^{128}$ are each independently a functional group having a COOH group or $PO(OH)_2$, a functional group to which a COOH group or $PO(OH)_2$ is bonded via π conjugation, hydrogen, an OH group, a methoxy group, halogen, an alkyl group having 1 to 30 carbon atoms, an alkoxy group, an amino group, a cyano group, or a nitro group.

The present invention also relates to the foregoing photosensitizer wherein in formula (I) $L^1$ contains a functional group having at least one COOH group or $PO(OH)_2$ or a functional group to which a COOH group or $PO(OH)_2$ is bonded via π conjugation, $L^2$ does not contain a COOH group or $PO(OH)_2$, and when the photosensitizer is adsorbed on a metal oxide semiconductor electrode via $L^1$, the energy level of $L^2$ in its excited state is higher than that of $L^1$ by at least 0.25 eV or more.

The present invention also relates to a photovoltaic device having at least one metal oxide semiconductor layer, wherein the metal oxide semiconductor layer comprises any of the foregoing photosensitizers.

Advantageous Effects of Invention

The novel photosensitizer of the present invention absorbs light in a wide visible region and can, therefore, enhance the conversion efficiency of a photovoltaic device.

BRIEF DESCRIPTION OF DRAWINGS

FIG. 4 is a graph showing the incident photo-to-current conversion efficiencies (IPCE) of Examples 1 to 4 and Comparative Example 1.

BEST MODE FOR CARRYING OUT THE INVENTION

Figure 1:
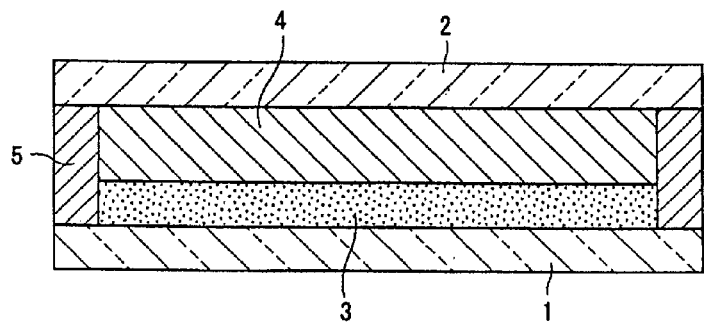
FIG. 1 is a cross-sectional view of an photovoltaic device.

The present invention will be described in detail below.
The photosensitizer of the present invention is a metal oxide represented by the following general formula (I):

$$ML^1L^2X_2 \qquad (I).$$

In formula (I), M represents a group 8 transition metal of the periodic table and may be Ru, Os, and Fe but is preferably Ru.

In formula (I), Xs are each independently a halogen atom, a cyano group, a thiocyanate group, an isothiocyanate group, an isocyanate group, an isocyanide group or a hydroxyl group, or a bidentate ligand represented by formula (A) if Xs are bonded to one another.

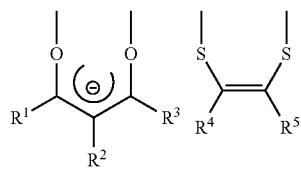

(A)

In formula (A), $R^1$ through $R^3$ may be the same or different from each other and are each independently hydrogen, an alkyl group having 1 to 30 carbon atoms, an alkoxyalkyl group having 2 to 30 carbon atoms, a perfluoroalkyl group having 1 to 30 carbon atoms, an aryl group having 6 to 30 carbon atoms, or an aralkyl group having 7 to 30 carbon atoms, and $R^4$ and $R^5$ are each independently hydrogen, a cyano group, an alkyl group having 1 to 20 carbon atoms, a perfluoroalkyl group having 1 to 20 carbon atoms, or an aryl group having 6 to 15 carbon atoms and may be bonded to one another to form a ring.

Specific examples of ligands represented by formula (A) are given below but are not limited thereto.

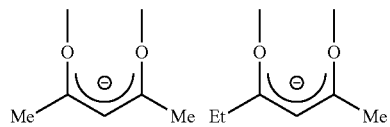

-continued

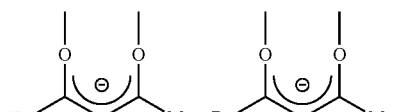

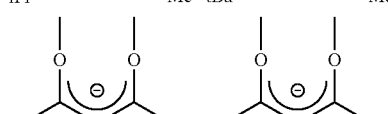

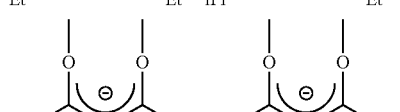

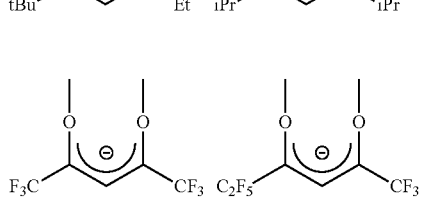

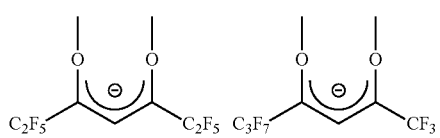

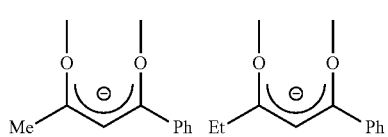

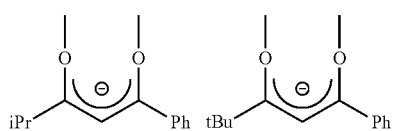

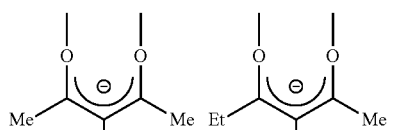

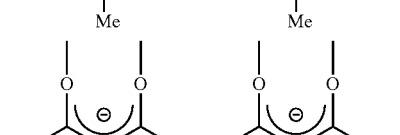

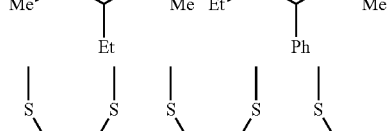

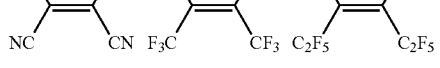

Examples of ligand $L^1$ include compounds represented by formula (II) below.

(II)

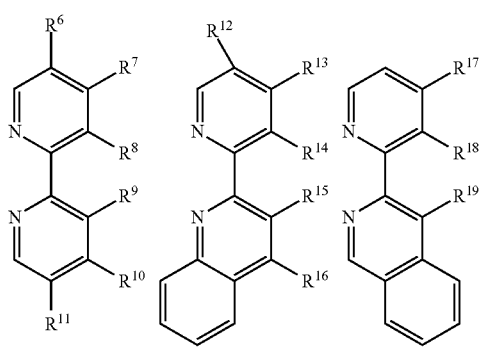
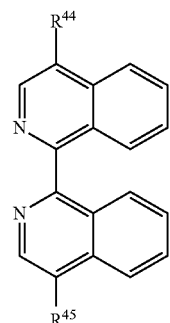

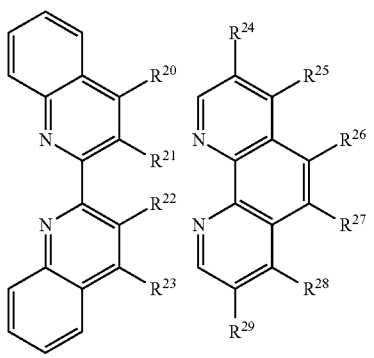

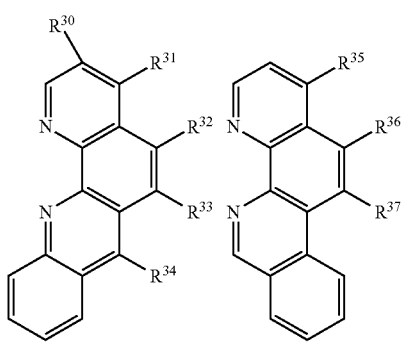

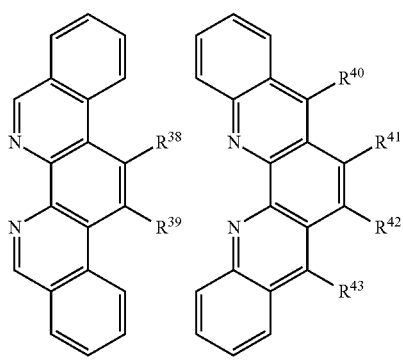

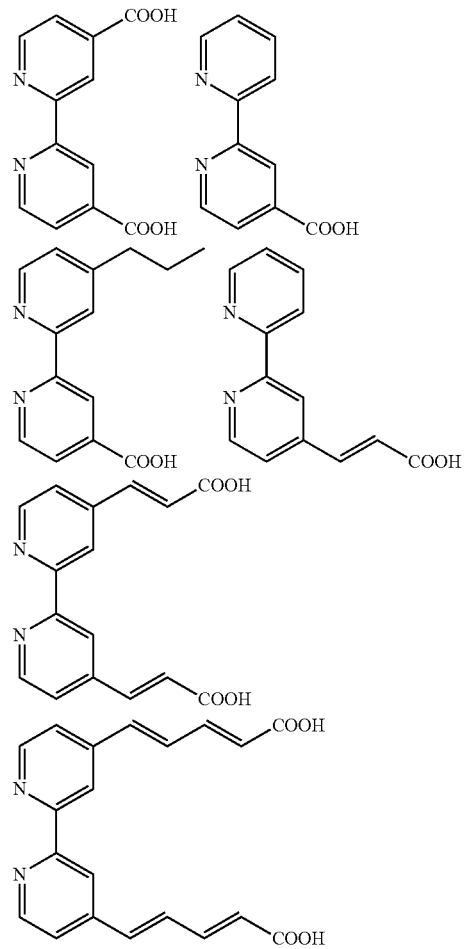

In formula (II), $R^6$ through $R^{11}$, $R^{12}$ through $R^{16}$, $R^{17}$ through $R^{19}$, $R^{20}$ through $R^{23}$, $R^{24}$ through $R^{29}$, $R^{30}$ through $R^{34}$, $R^{35}$ through $R^{37}$, $R^{38}$ through $R^{39}$, $R^{40}$ through $R^{43}$, and $R^{44}$ through $R^{45}$ may be the same or different from each other and are each independently a functional group having a COOH group or $PO(OH)_2$, a functional group to which a COOH group or $PO(OH)_2$ is bonded via π conjugation, hydrogen, an alkyl group having 1 to 30 carbon atoms, an alkenyl group, aryl group, an alkoxy group, or an amino group.

Specific examples of compounds represented by formulas (II) are given below but not limited thereto.

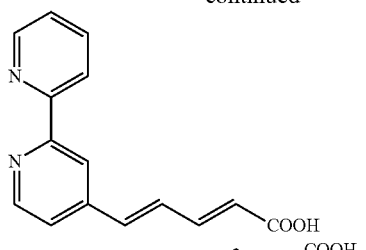
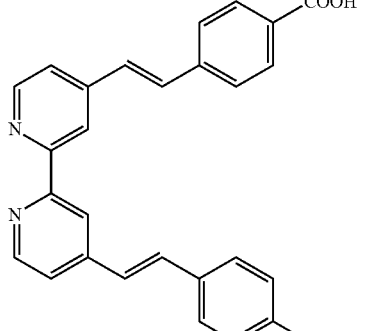
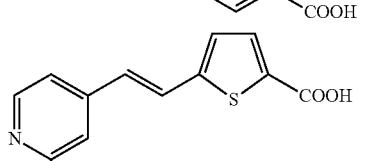
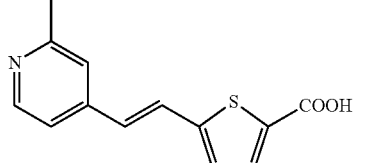
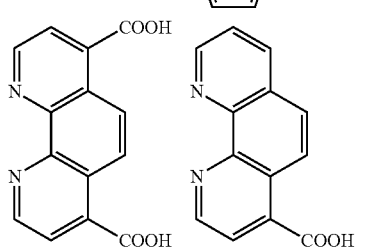
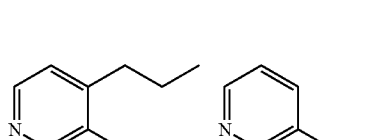
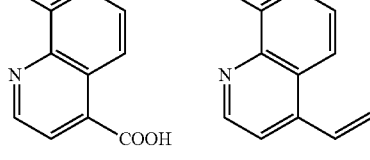
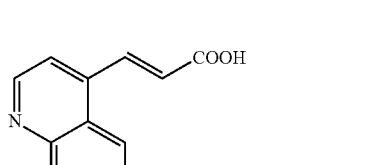
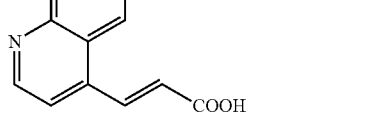
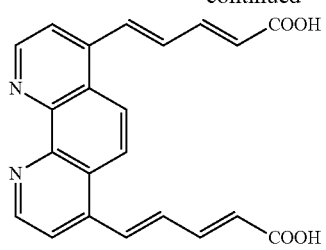
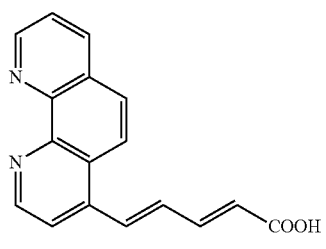
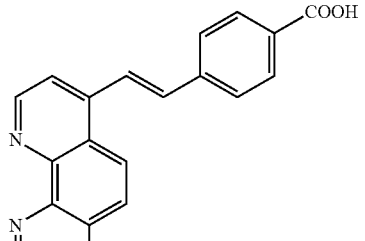
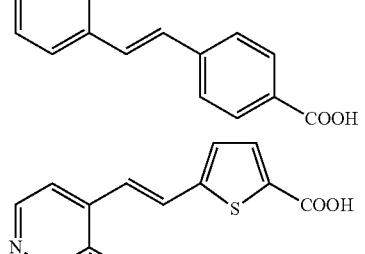
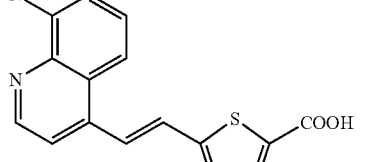
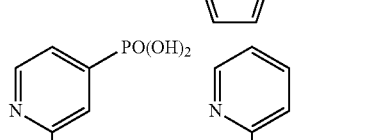
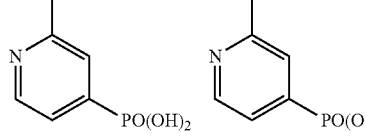
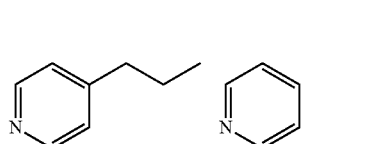
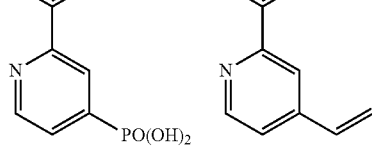

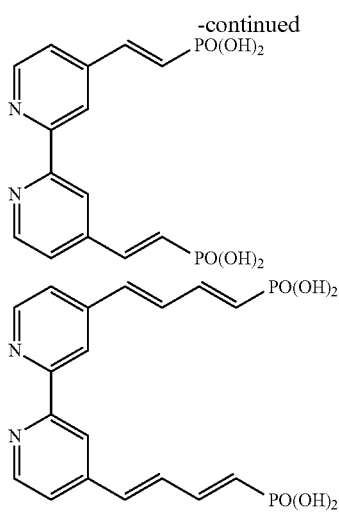
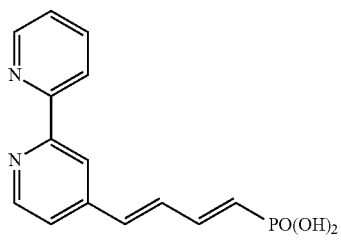
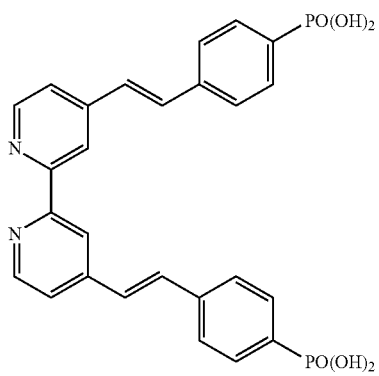
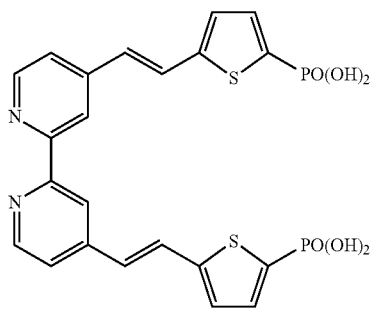

Examples of ligand $L^2$ include compounds represented by formula (III) below.

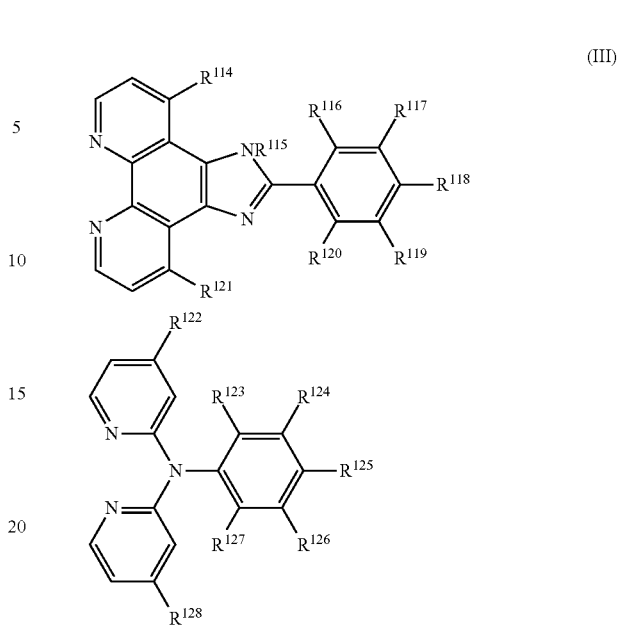

In formula (III), $R^{114}$ through $R^{128}$ are each independently a functional group having a COOH group or $PO(OH)_2$, a functional group to which a COOH group or $PO(OH)_2$ is bonded via π conjugation, hydrogen, an OH group, a methoxy group, halogen, an alkyl group having 1 to 30 carbon atoms, an alkoxy group, an amino group, a cyano group, or a nitro group.

Specific examples of compounds represented by formula (III) are given below but not limited thereto.

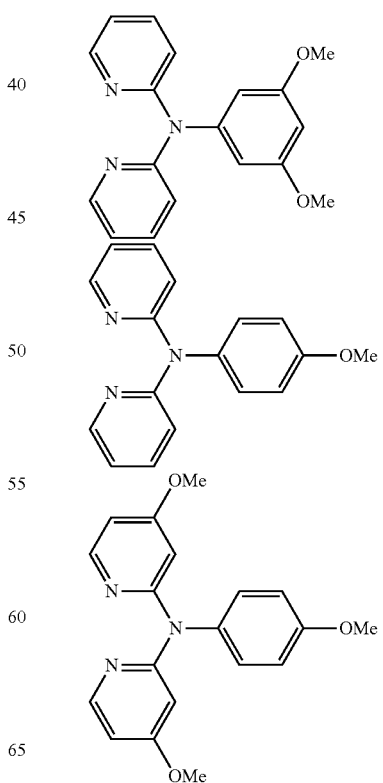

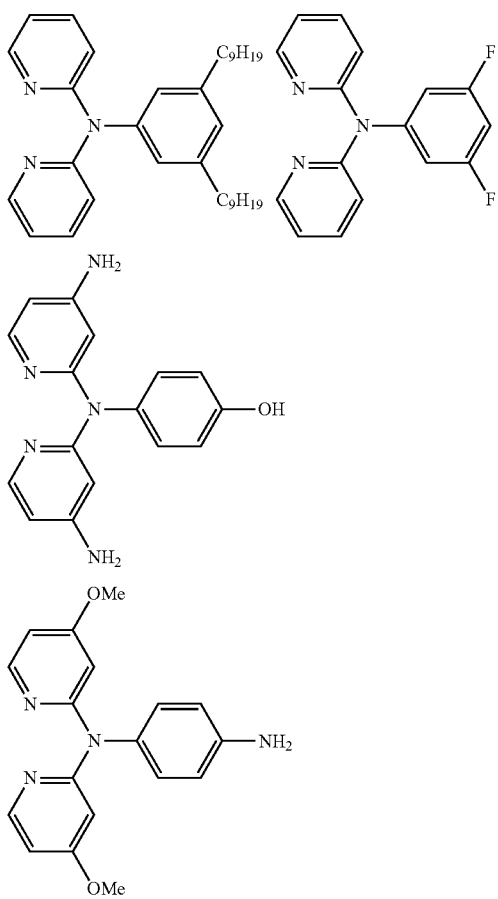
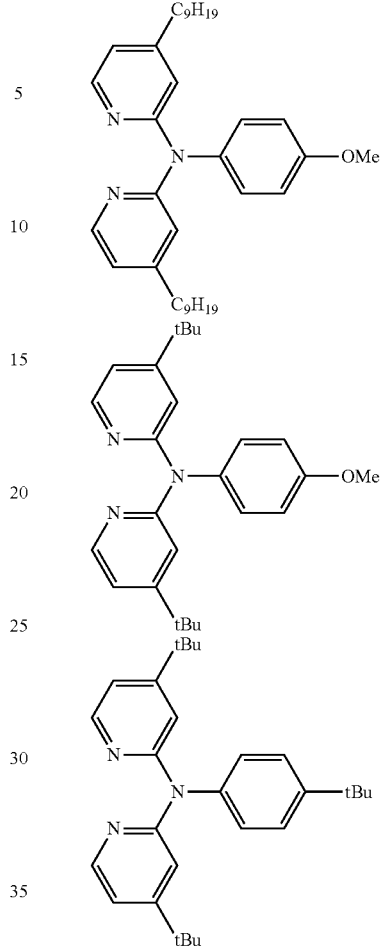

In a photosensitizer comprising a metal complex represented by formula (I) according to the present invention for metal oxide semiconductor electrodes, $L^1$ and $L^2$ necessarily fulfill the following requirements.

That is, the photosensitizer is adsorbed on a metal oxide semiconductor electrode via ligand $L^1$ or $L^2$ whichever is lower in energy level in its excited state than the other, and both of the ligands are positioned higher than the energy level of conduction band of the metal oxide semiconductor electrode. In the present invention, when the photosensitizer is adsorbed on the metal oxide semiconductor electrode via ligand $L^1$ or $L^2$, the difference $\Delta L$ between the energy levels of ligands $L^1$ and $L^2$ in their excited states calculated in accordance with a GAUSSIAN03 quantum chemistry calculation program is necessarily 0.25 eV or more, preferably 0.3 eV or more.

If the difference $\Delta L$ is less than 0.25 eV, the electrons excited to ligand $L^1$ or $L^2$ whichever is higher in energy level in its exited state than the other, can not move to the lower energy level ligand which is adsorbed on the metal oxide and thus is unlikely to be injected into the metal oxide semiconductor electrode, resulting in a decrease in conversion efficiency.

There is no particular restriction imposed on the GAUSSIAN03 quantum chemistry program calculation, which is, however, generally carried out with reference to "Johokagaku/Keisankagaku Jikken" (Kenji Hori et. al., Maruzen Kabushiki Kaisha).

That is, the program calculation is carried out by DFT/TD-DFT calculation using supercomputer HP2500, considering a solvent (ethanol) using CPCM solvent model. With regard to structure optimization and electron structure/molecular orbit energy level, the calculation is carried out using DFT/B3LYP calculation method and LANL2DZ basis function.

Examples of compounds (photosensitizers) represented by formula (I) fulfilling the above requirements include the following compounds but are not limited thereto.

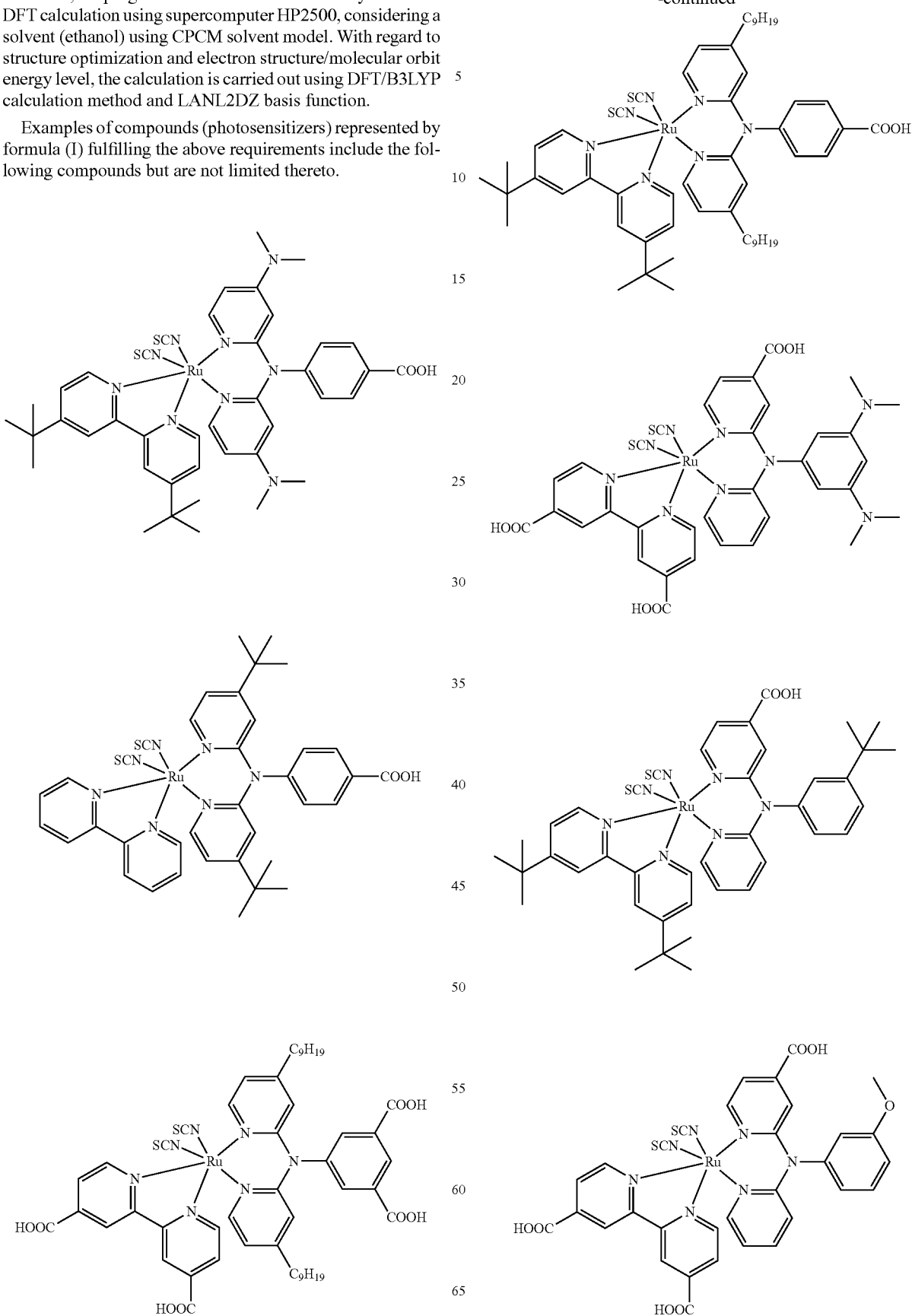

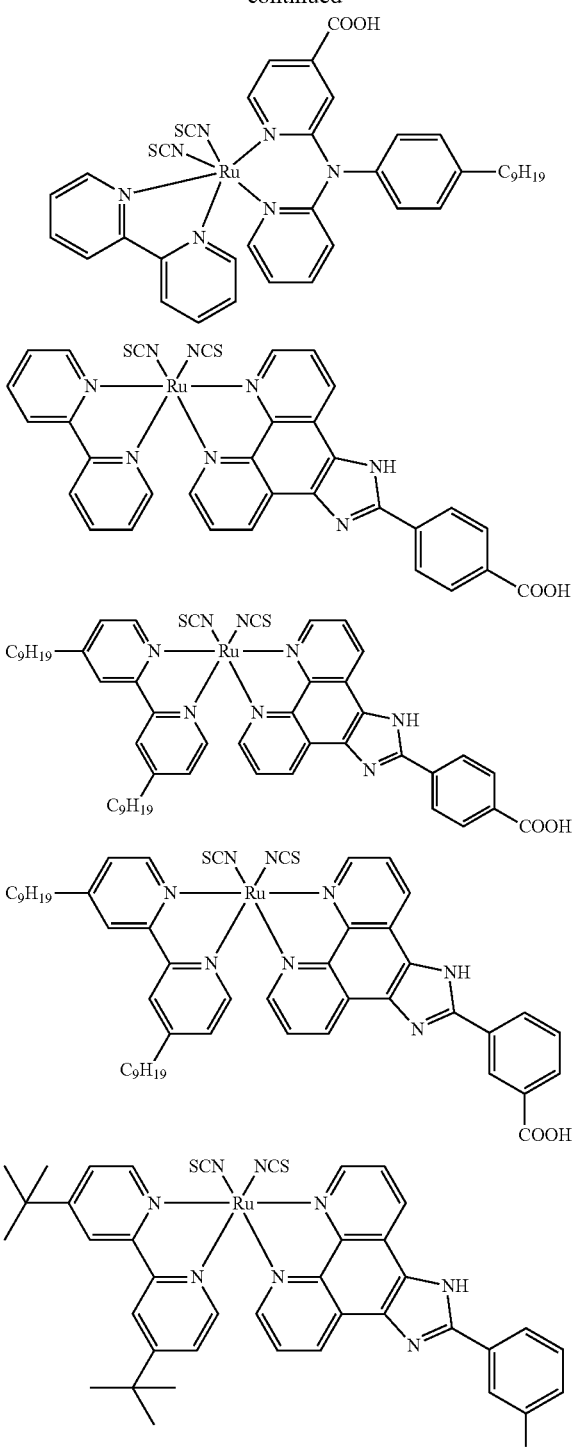
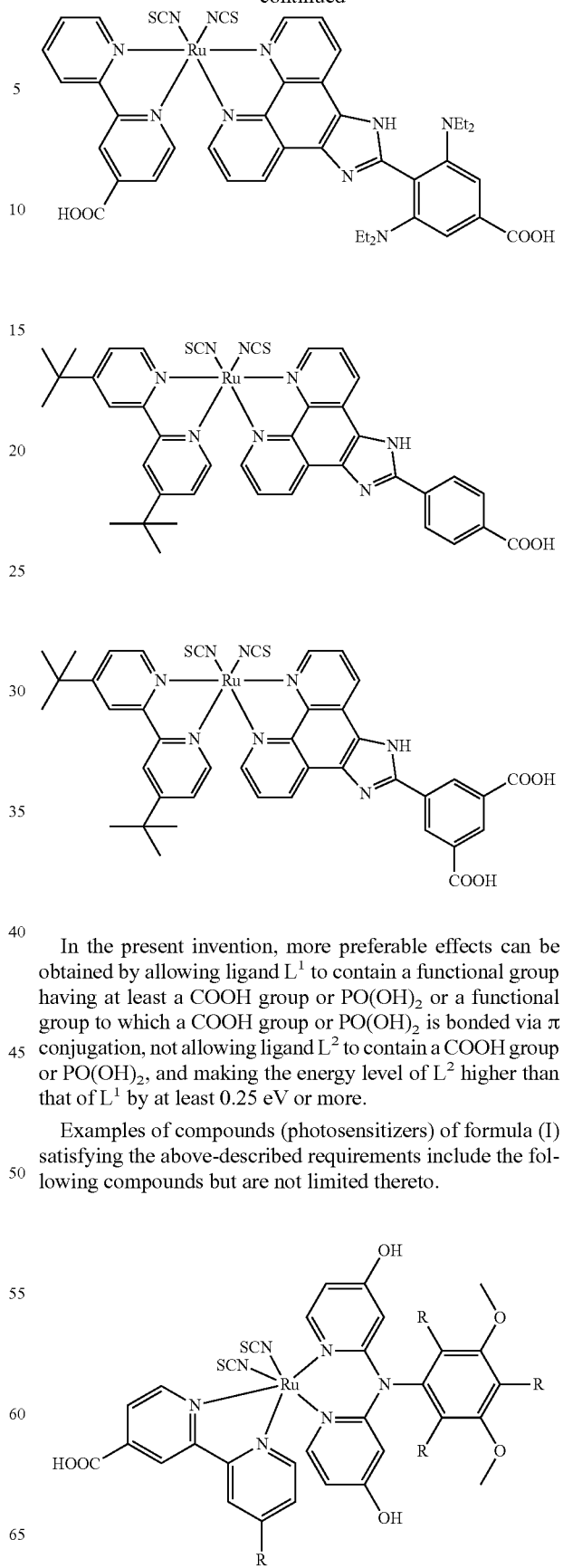

In the present invention, more preferable effects can be obtained by allowing ligand $L^1$ to contain a functional group having at least a COOH group or $PO(OH)_2$ or a functional group to which a COOH group or $PO(OH)_2$ is bonded via π conjugation, not allowing ligand $L^2$ to contain a COOH group or $PO(OH)_2$, and making the energy level of $L^2$ higher than that of $L^1$ by at least 0.25 eV or more.

Examples of compounds (photosensitizers) of formula (I) satisfying the above-described requirements include the following compounds but are not limited thereto.

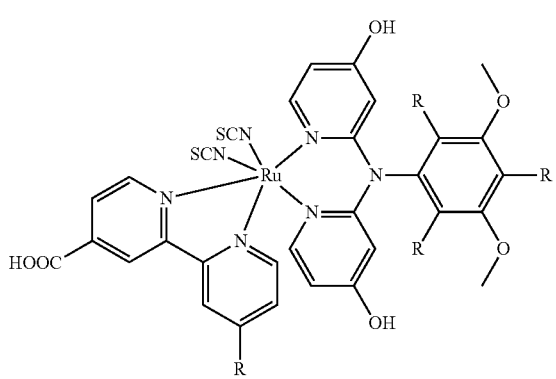

-continued
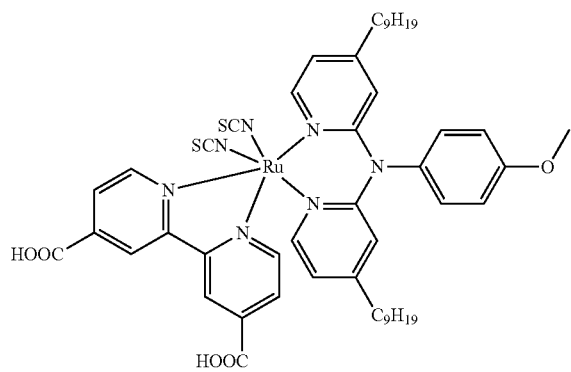
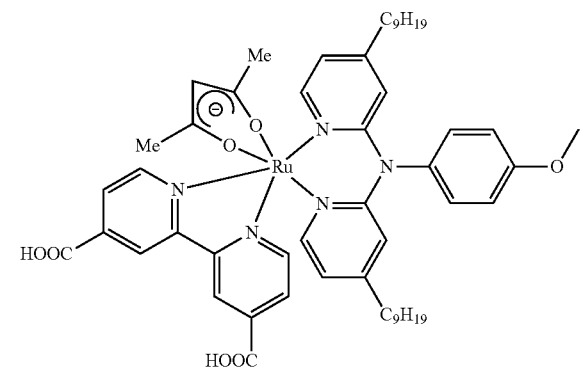
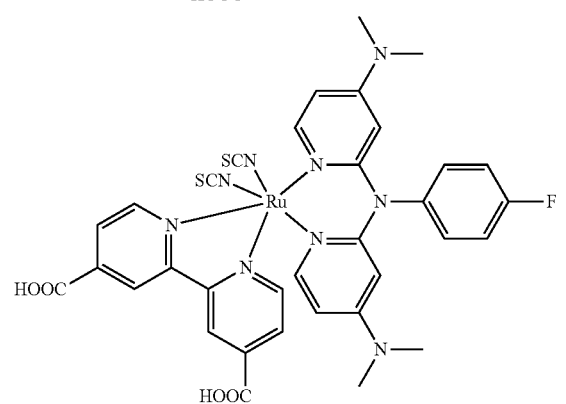
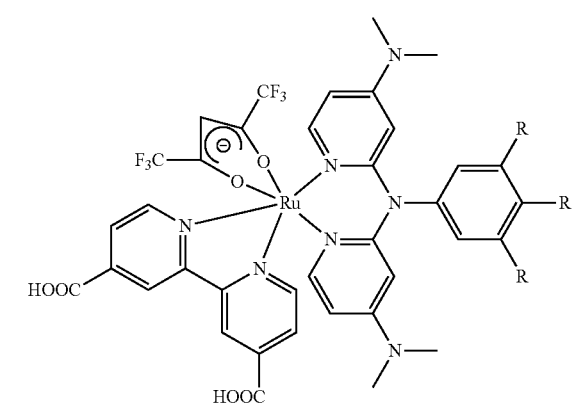
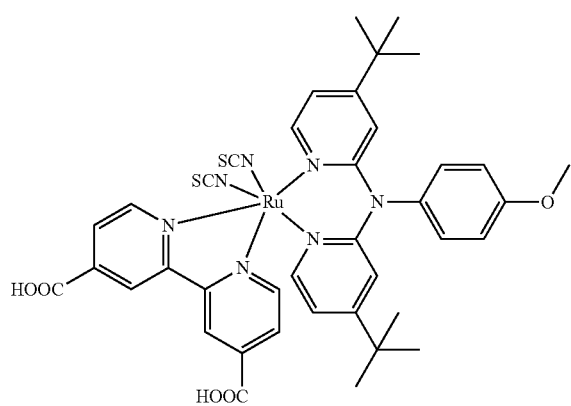
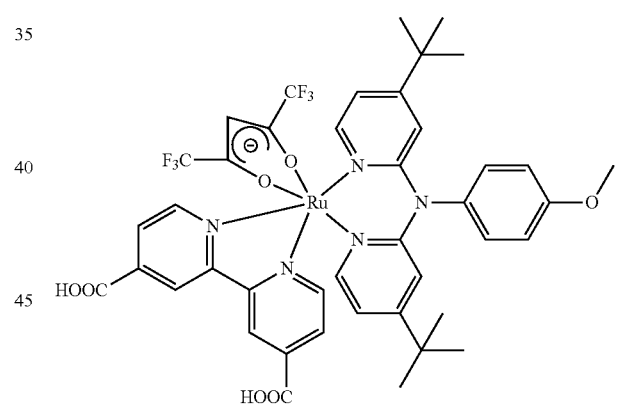
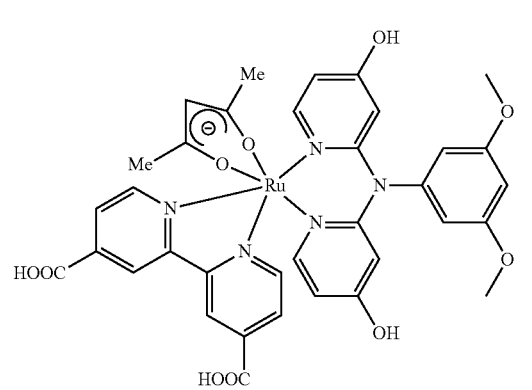
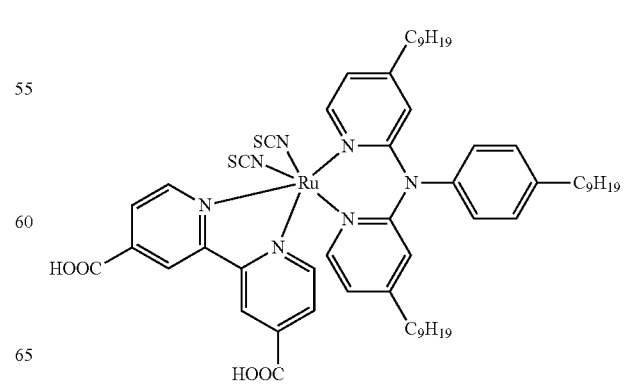

-continued
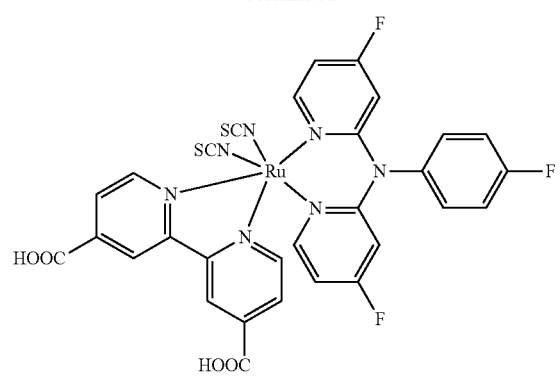
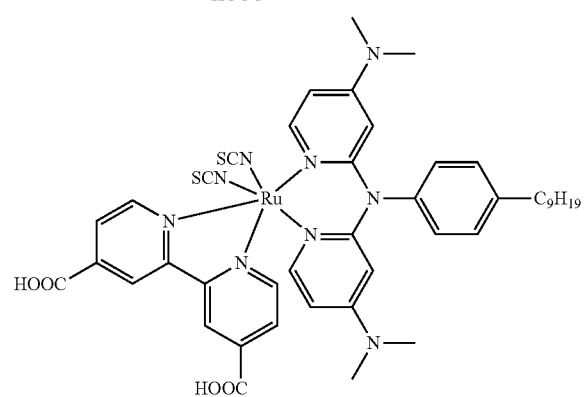
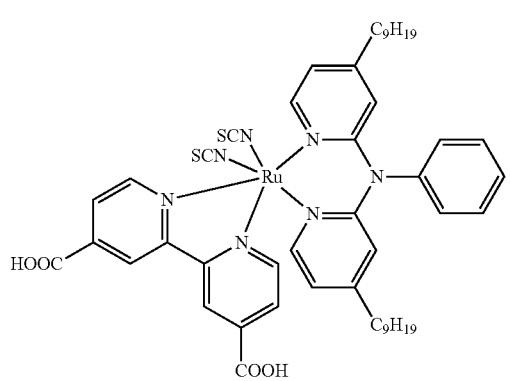
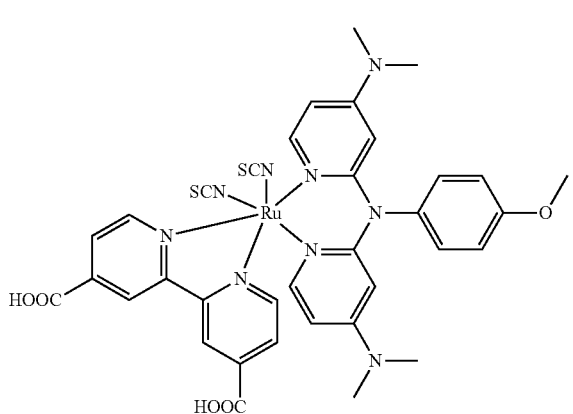
-continued
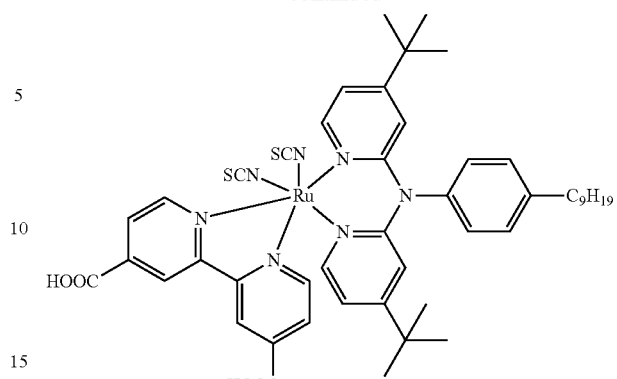
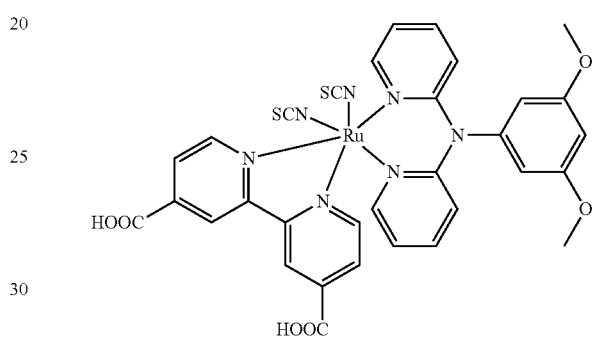
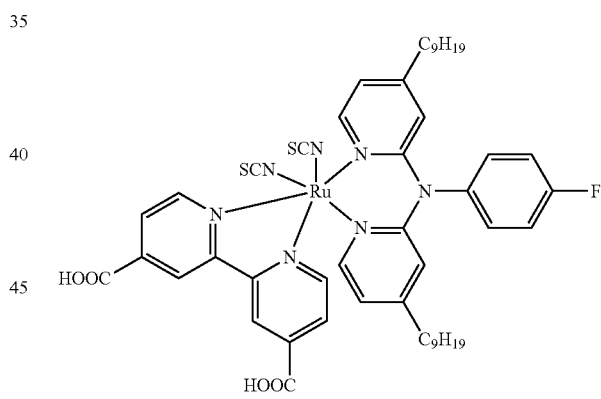
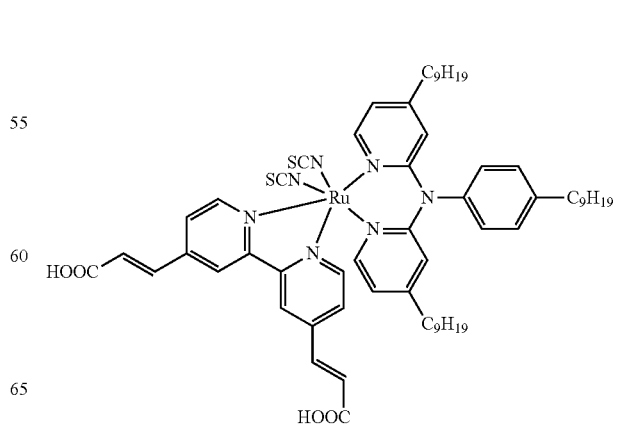

-continued
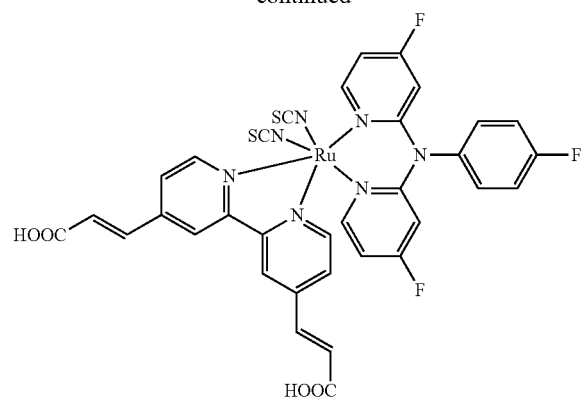
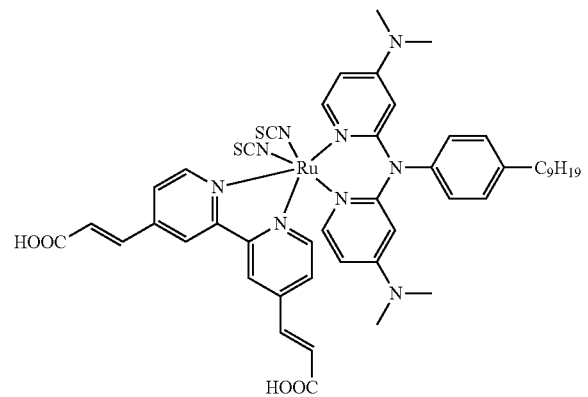
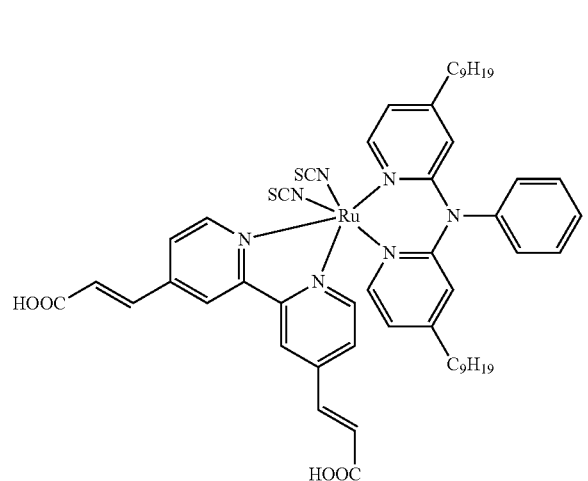
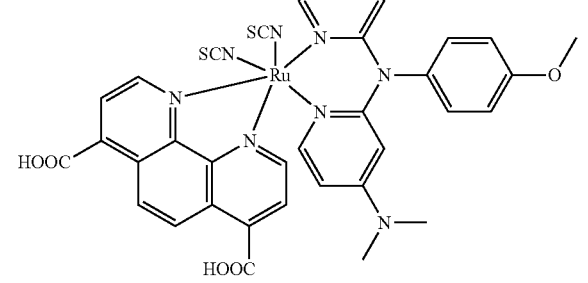
-continued
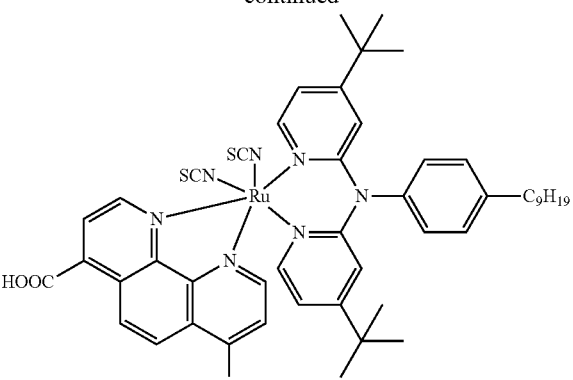
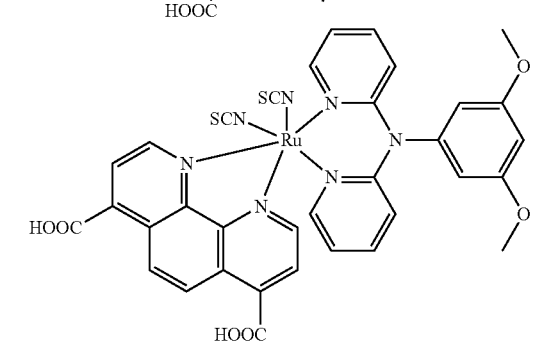
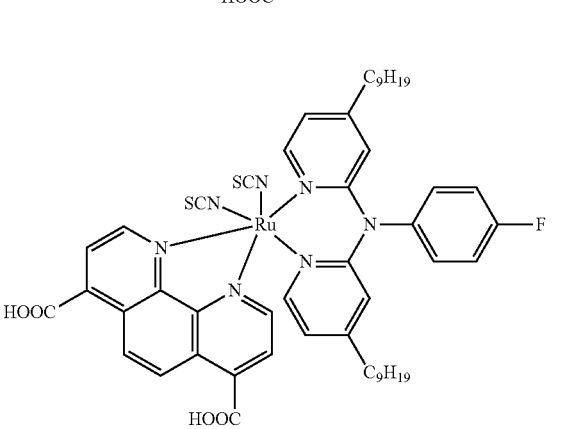
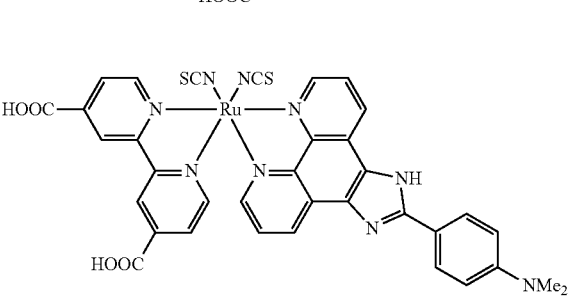
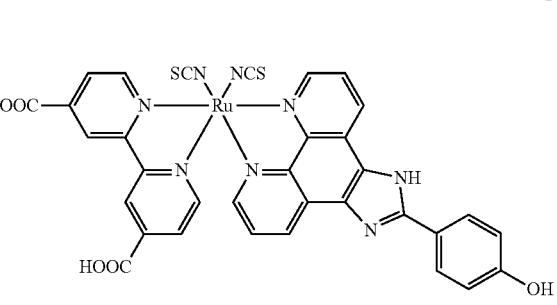

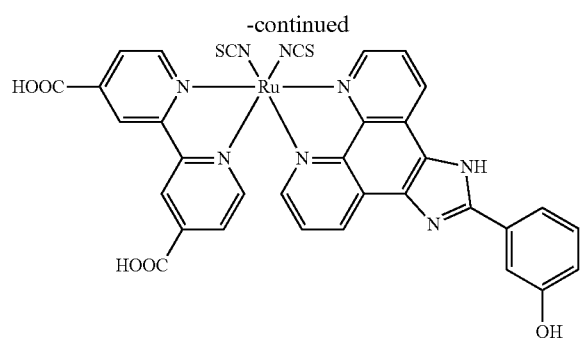
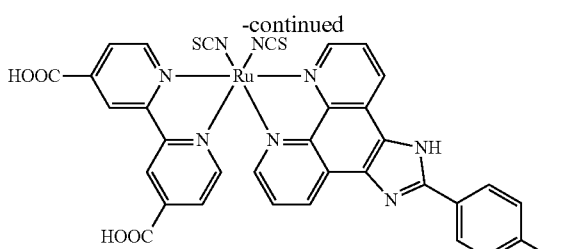
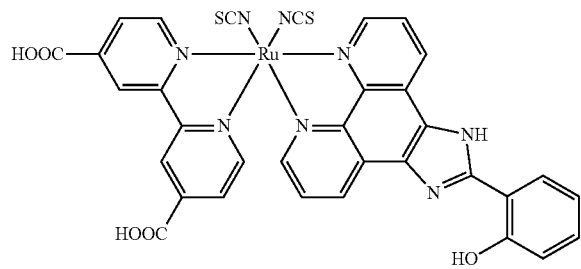
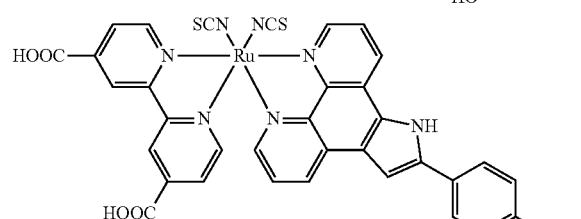
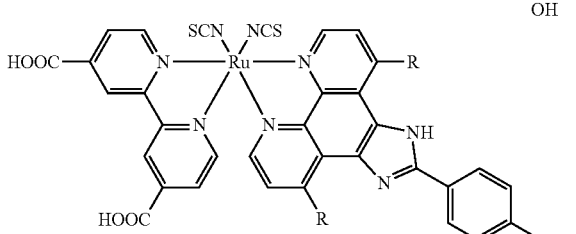
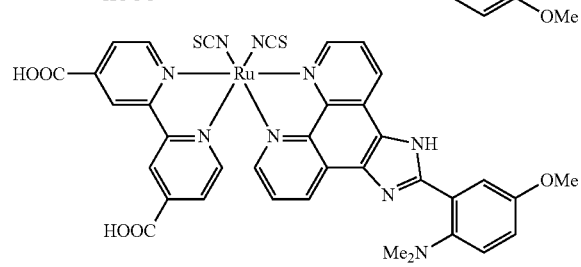
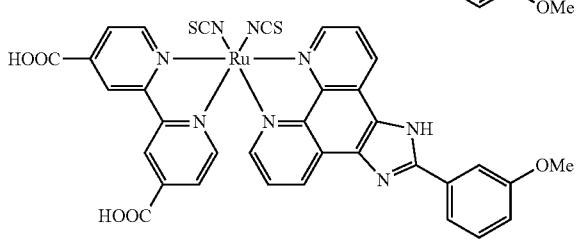
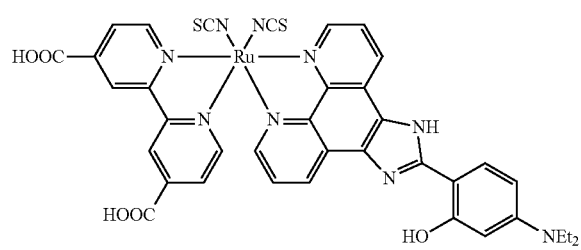
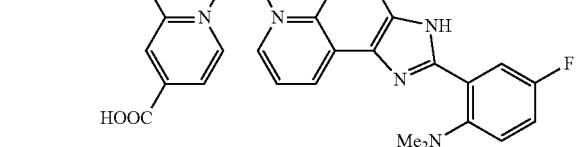
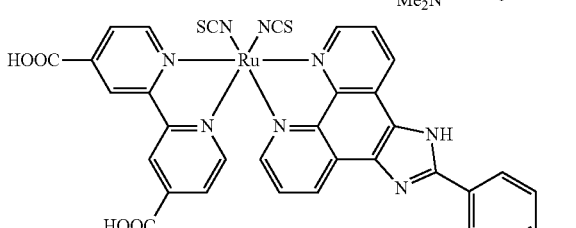
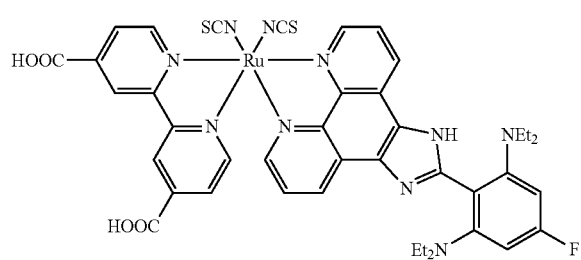
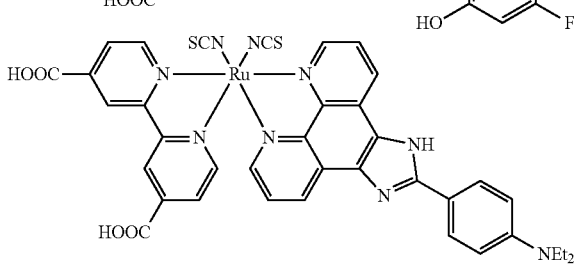

-continued

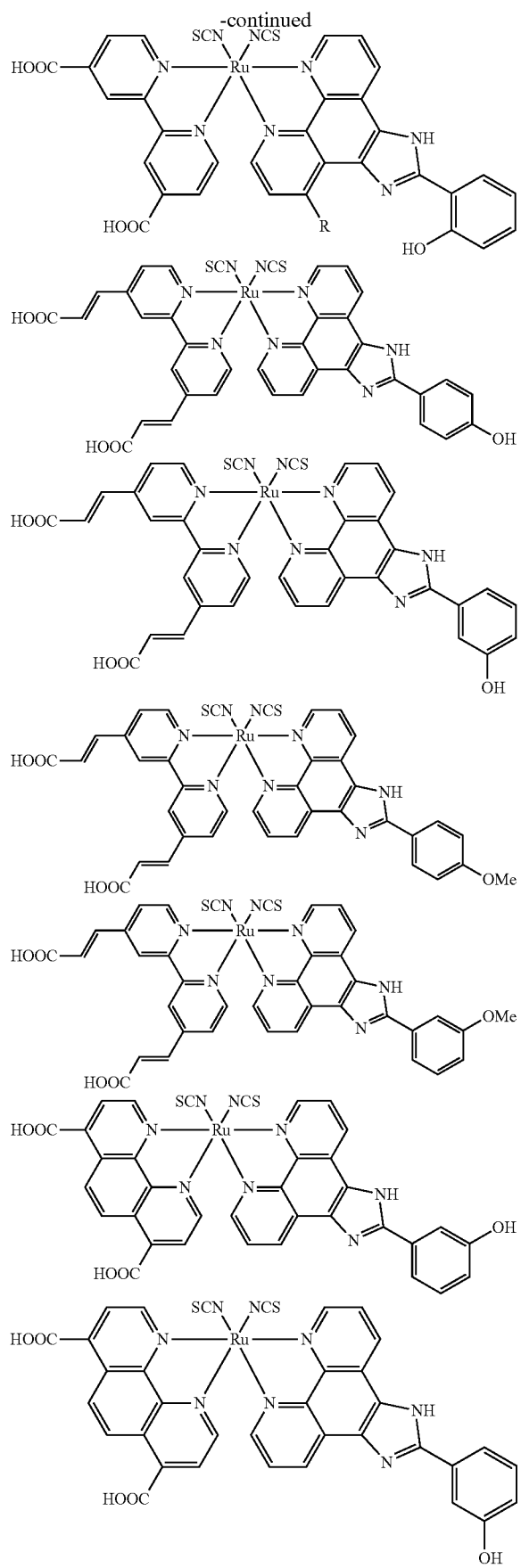

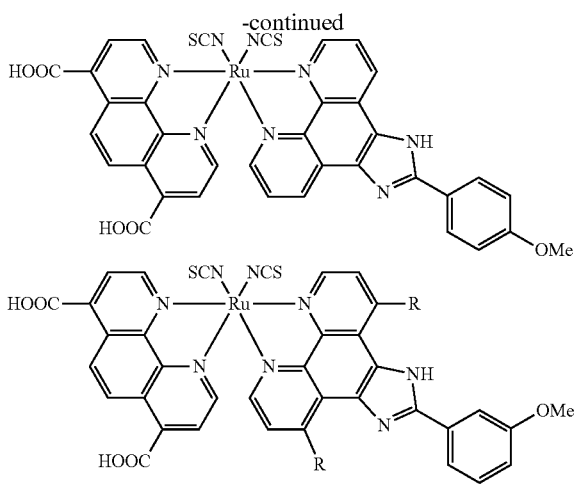

An explanation will be given of a method for synthesizing the photosensitizer of the present invention.

The explanation will be made with reference to an example wherein ruthenium is used as M in formula (I). First of all, a method is preferably used wherein a ruthenium precursor is reacted with ligands $L^1$ and $L^2$ successively and then X is introduced thereto. Examples of the ruthenium precursor include ruthenium chloride, dichloro(p-cymen)ruthenium dimmer, and diiodine(p-cymen)ruthenium dimmer. The reaction may be carried out by adding $L^1$ and $L^2$ successively or simultaneously. For the successive reaction, either $L^1$ or $L^2$ may be added at first.

A reaction solvent may be a conventional organic solvent or water, and is preferably alcohol solvents such as methanol, ethanol, and butanol, amide solvents such as dimethyl formaimde and dimethyl acetamide, and polar solvents such as dimethyl sulfoxide, propylene carbonate, and N-methylpyrrolidone.

No particular limitation is imposed on the reaction temperature. However, the reaction is preferably carried out by heating particularly preferably at a temperature within the range of 50 to 250° C. When the reaction is carried out successively, the reaction temperatures in the first stage and second stage reactions may be varied. Heating may be carried out using an oil bath, a water bath, or a microwave heating device.

No particular limitation is imposed on the reaction time. However, it is usually from one minute to a few days, preferably from 5 minutes to one day and is preferably changed with a heating device.

With regard to X, it can be introduced by adding a corresponding ammonium salt or metal salt into the system to be reacted. No particular limitation is imposed on the reaction time or temperature.

Next, the photovoltaic device of the present invention will be described.

Examples of the photovoltaic device of the present invention include a device having a cross-section as shown in FIG. 1. This device has a metal oxide semiconductor layer 3 on which the photosensitizer is adsorbed, disposed on a transparent electrically conductive substrate 1, and an electrolyte layer 4 disposed between the metal oxide semiconductor layer 3 and a counter electrode substrate 2. The periphery of the device is sealed with a sealant 5. Lead wires are connected to the electrically conductive portions of the transparent substrate 1 and counter electrode substrate 2 so as to obtain electric power.

The transparent electrically conductive substrate is generally manufactured by laminating a transparent electrode layer over a transparent substrate. No particular limitation is imposed on the transparent substrate. The material, thickness, dimension, shape of the transparent substrate may be appropriately selected depending on the purposes. Examples of the transparent substrate include colored or colorless glasses, wire glasses, glass blocks, and colored or colorless transparent resins. Specific examples of such resins include polyesters such as polyethylene terephthalate, polyamides, polysulfones, polyethersulfones, polyether ether ketones, polyphenylene sulfides, polycarbonates, polyimides, polymethyl methacrylates, polystyrenes, cellulose triacetates, and polymethyl pentenes. The definition "transparent" used herein refers to a transparency of 10 to 100 percent. The substrates used herein are those having a smooth surface at ordinary temperature, which surface may be flat or curved or deformed with stress.

No particular limitation is imposed on the transparent electrically conductive layer for forming the electrically conductive layer of the electrode as long as it can achieve the purposes of the present invention. Examples of the transparent electrically conductive layer include metal films of gold, silver, chrome, copper and tungsten and electrically conductive films of metal oxides. Examples of the metal oxides include those produced by doping tin oxide or zinc oxide with a small amount of other metal element, such as indium tin oxide ($ITO(In_2O_3:Sn)$), fluorine doped tin oxide ($FTO(SnO_2:F)$) and aluminum doped zinc oxide ($AZO(ZnO:Al)$).

The film thickness is usually from 10 nm to 10 μm, preferably from 100 nm to 2 μm. The surface resistance (resistivity) is properly selected depending on the use of the substrate in the present invention, but is usually from 0.5 to 500 Ω/sq, preferably from 2 to 50 Ω/sq.

The counter electrode is usually a platinum or carbon electrode. No particular limitation is imposed on the material of the substrate of the counter electrode. The material, thickness, dimension, shape of the substrate may be appropriately selected depending on the purposes. Examples of the substrate include colored or colorless glasses, wire glasses, glass blocks, and colored or colorless transparent resins. Specific examples of such resins include polyesters such as polyethylene terephthalate, polyamides, polysulfones, polyethersulfones, polyether ether ketones, polyphenylene sulfides, polycarbonates, polyimides, polymethylmethacrylates, polystyrenes, cellulose triacetates, and polymethyl pentenes. Alternatively, a metal plate may be used as a substrate.

No particular limitation is imposed on the metal oxide semiconductor layer. Examples include layers of $TiO_2$, $ZnO$, $SnO_2$, and $Nb_2O_5$. Amongst, layers of $TiO_2$ and $ZnO$ are preferable.

The semiconductor used in the present invention may be monocrystal or polycrystal. The crystal system may be selected from those of anatase, rutile, and brookite type, among which preferred are those of anatase type.

Any conventional method may be used for forming the metal oxide semiconductor layer. For example, the layer may be produced by coating a nano-particle dispersant or sol solution of the metal oxide semiconductor layer over a substrate in a conventional manner. No particular limitation is imposed on the coating method. Examples of the method include various methods such as casting method for forming a film, spin-coating, dip-coating, bar-coating, and screen printing methods.

The thickness of the metal oxide semiconductor layer can be arbitrarily selected but is usually from 0.5 to 50 μm, preferably from 1 to 20 μm.

The photosensitizer of the present invention may be adsorbed on a metal oxide semiconductor layer, for example, by spray or spin coating thereon a solution wherein the photosensitizer is dissolved in a solvent and then drying the solution. In this case, the substrate may be heated to an appropriate temperature. Alternatively, a method may be used wherein the metal oxide semiconductor layer is immersed in a solution wherein the photosensitizer is dissolved in a solvent to allow the photosensitizer to be adsorbed thereon. No particular limitation is imposed on the time for immersing if the photosensitizer is adsorbed sufficiently. However, the immersing time is preferably from 10 minutes to 30 hours, more preferably from 1 to 20 hours. If necessary, the solvent or substrate may be heated upon immersion. The concentration of the photosensitizer in a solution is from 0.01 to 100 mmol/L, preferably from 0.1 to 50 mmol/L.

Examples of the solvent include alcohols, ethers, nitriles, esters, and hydrocarbons.

In order to reduce interactions of the photosensitizers such as coagulation, a colorless compounds with properties of surfactant may be added to be co-adsorbed on the metal oxide semiconductor layer. Examples of such a colorless compound include those having a carboxyl group or a sulfo group, including steroid compounds such as cholic acid, deoxycholic acid, chenodexycholic acid, and taurodexycholic acid and sulfonic acid salts.

The unadsorbed photosensitizer is preferably washed out immediately after completion of the adsorption step. Washing is preferably carried out in a wet type washing bath using an acetnitrile or alcohol solvent.

The adsorbed amount of the photosensitizer is determined by desorbing the photosensitizer from the metal oxide semiconductor layer with a strong alkali solution and then calculating the light absorption of the alkali solution.

The photosensitizer can be adsorbed in an amount of $1.0 \times 10^{-8}$ to $1.0 \times 10^{-6}$ mol/cm$^2$ on the basis of the surface area of the metal oxide semiconductor layer.

After allowing the photosensitzer to adsorb, the metal oxide semiconductor layer may be surface-treated using any of amines, quaternary ammonium salts, ureide compounds having at least one ureide group, silyl compounds having at least one silyl group, alkali metal salts, and alkaline earth metal salts. Preferable examples of the amines include pyridine, 4-t-butylpyridine, and polyvinylpyridine. Preferable examples of the quaternary ammonium salts include tetrabutylammonium iodine and tetrahexylammonium iodine. These may be dissolved in an organic solvent before use or used as they are if they are liquid.

No particular limitation is imposed on the electrolyte used in the photovoltaic device of the present invention. The electrolyte may be liquid or solid and preferably exhibits reversible electrochemical oxidation-reduction properties. Exhibiting reversible electrochemical oxidation-reduction properties refers to enabling the occurrence of a reversible electrochemical oxidation-reduction reaction in a potential region wherein a photovoltaic device acts. The electrolyte is reversible preferably in the potential region of −1 to +2 V vs NHE with respect to a normal hydrogen electrode (NHE).

The ion conductivity of the electrolyte is usually $1 \times 10^{-7}$ S/cm or higher, preferably $1 \times 10^{-6}$ S/cm or higher, more preferably $1 \times 10^{-5}$ S/cm or higher.

No particular limitation is imposed on the thickness of the electrolyte layer. However, the thickness is preferably 1 μm or more, more preferably 10 μm or more and preferably 3 mm or less, more preferably 1 mm or less.

No particular limitation is imposed on the electrolyte as long as the above requirements are satisfied. Liquid or solid electrolytes which are known in the field of the present invention may be used.

EXAMPLES

The present invention will be described in more details with reference to the following examples but is not limited thereto.

Example 1

Synthesis of Compound 1

1,10-phenanthroline-5,6-dione (10 mmol; 2.10 g), ammonium acetate (200 mmol; 14.4 g), and salicyl aldehyde (12 mmol; 1.45 g) were dissolved in 100 ml of acetic acid, and stirred while being heated and refluxed for 4 hours. After completion of the reaction, the mixture was allowed to cool and then neutralized with ammonia water. Precipitated deposit was separated by filtration and then washed with water and dried under reduced pressure thereby producing Compound 1 at a yield of 65 percent. Compound 1 was identified with NMR.

Synthesis of Photosensitizer 1

Dichloro(p-cymen)ruthenium dimmer (1 mmol; 0.61 g) and Compound 1 (2 mmol; 0.65 g) were dissolved in dimethylformamide (50 ml), and then stirred at a temperature of 80° C. under an argon atmosphere for 2 hours. Thereafter, 2,2'-bipyridine-4,4'-carboxylic acid (2 mmol) was added to the mixture and stirred while being heated at a temperature of 150° C. under an argon atmosphere for 5 hours. Further, ammonium thiocyanate (1.5 g) was added to the mixture and stirred while being heated for 4 hours.

Figure 2:
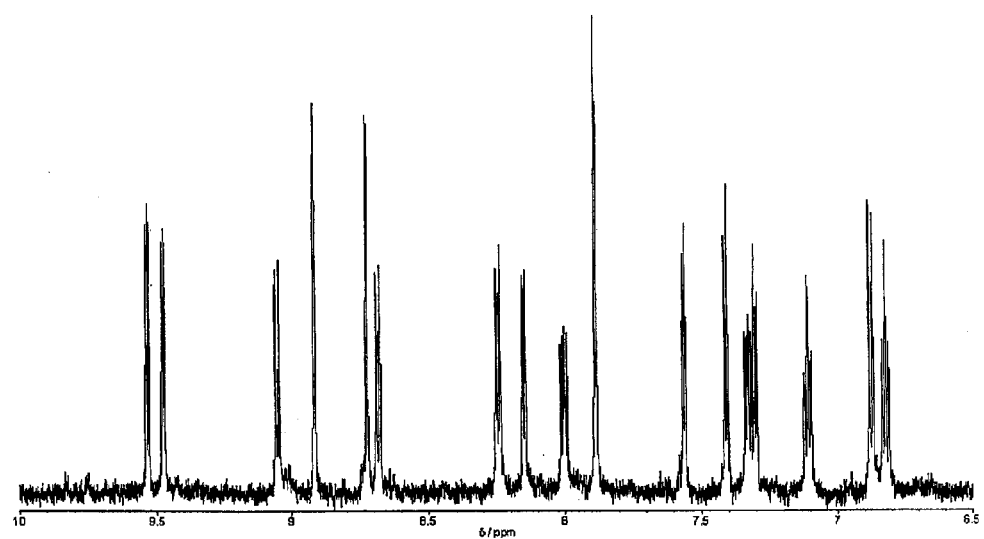
FIG. 2 is an $^1$H-NMR spectrum of Photosensitizer 1.

After completion of the reaction, the mixture was vacuum-concentrated and the resulting residue was dispersed in water and filtered thereby producing an intended product in the form of a crude refined product. An aqueous solution of n-butylammonium hydroxide was added in methanol and the intended product was dissolved therein, and then refined with a column (Sephadex LH-20). After the main component thus obtained was vacuum-concentrated, it was diluted with water and made at a pH of 2 with an aqueous solution of diluted $HNO_3$. The resulting deep red deposit was recovered by filtration and then vacuum-dried thereby producing intended Photosensitizer 1 at a yield of 70 percent. Photosensitizer 1 was identified with MS spectrum (m/z 386) and $^1$H-NMR spectrum. FIG. 2 shows the $^1$H-NMR spectrum of Photosensitizer 1.

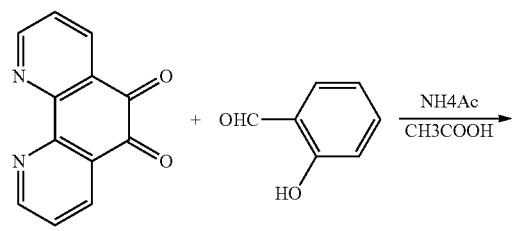

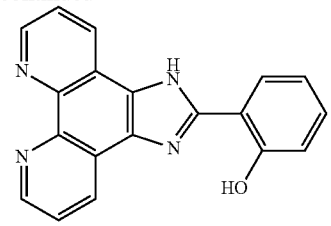

(Compound 1)

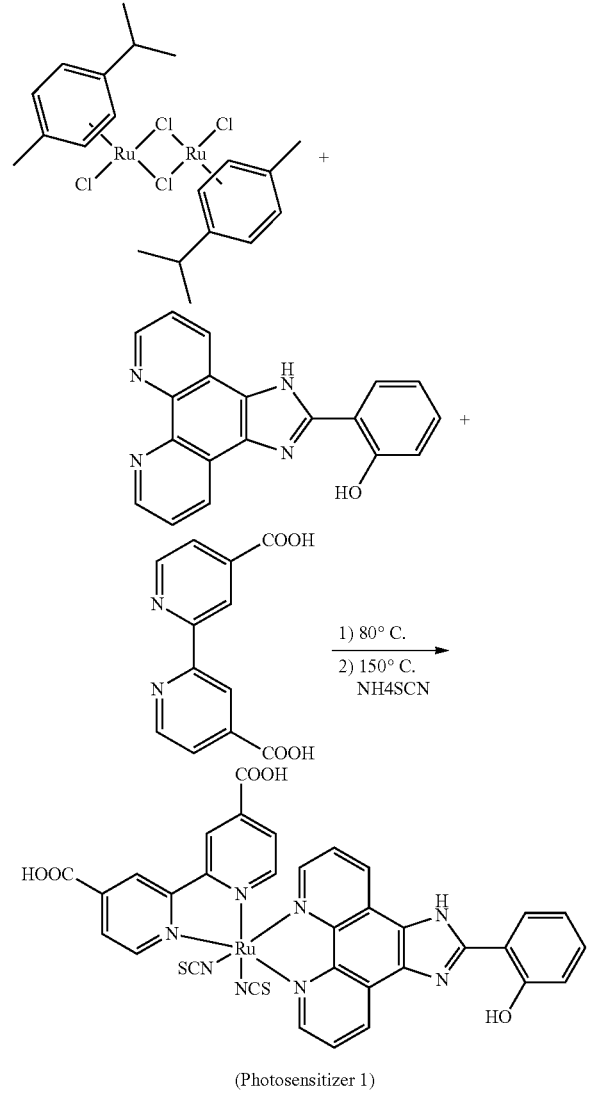

(Photosensitizer 1)

Example 2

Synthesis of Compound 2

1,10-phenanthroline-5,6-dione (10 mmol; 2.10 g), ammonium acetate (200 mmol; 14.4 g), and 3-hydroxybenzaldehyde (12 mmol; 1.45g) were dissolved in 100 ml of acetic acid, and stirred while being heated and refluxed for 4 hours. After completion of the reaction, the mixture was allowed to cool and then neutralized with ammonia water. Precipitated deposit was separated by filtration and then washed with water and dried under reduced pressure thereby producing Compound 2 at a yield of 65 percent. Compound 2 was identified with NMR.

Synthesis of Photosensitizer 2

Dichloro(p-cymen)ruthenium dimmer (1 mmol; 0.61 g) and Compound 2 (2 mmol; 0.65 g) were dissolved in dimethylformamide (50 ml), and then stirred at a temperature of 80° C. under an argon atmosphere for 2 hours. Thereafter, 2,2'-bipyridine-4,4'-carboxylic acid (2 mmol) was added to the mixture and stirred while being heated at a temperature of 150° C. under an argon atmosphere for 5 hours. Further, ammonium thiocyanate (1.5 g) was added to the mixture and stirred while being heated for 4 hours.

After completion of the reaction, the mixture was vacuum-concentrated and the resulting residue was dispersed in water and filtered thereby producing an intended product in the form of a crude refined product. An aqueous solution of n-butylammonium hydroxide was added in methanol and the intended product was dissolved therein, and then refined with a column (Sephadex LH-20). After the main component thus obtained was vacuum-concentrated, it was diluted with water and made at a pH of 2 with an aqueous solution of diluted $HNO_3$. The resulting deep red deposit was recovered by filtration and then vacuum-dried thereby producing intended Photosensitizer 2 at a yield of 70 percent. Photosensitizer 2 was identified with MS spectrum (m/z 386) and $^1$H-NMR spectrum.

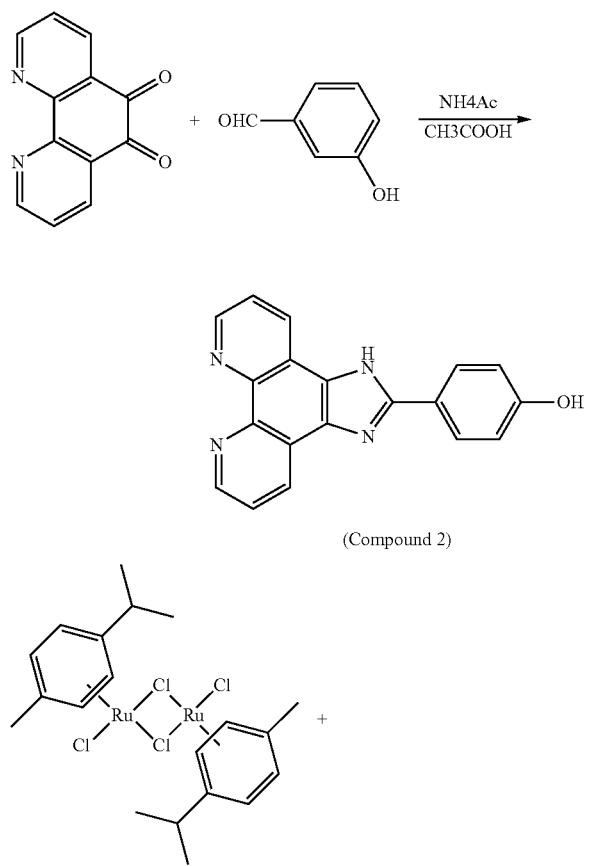

(Compound 2)

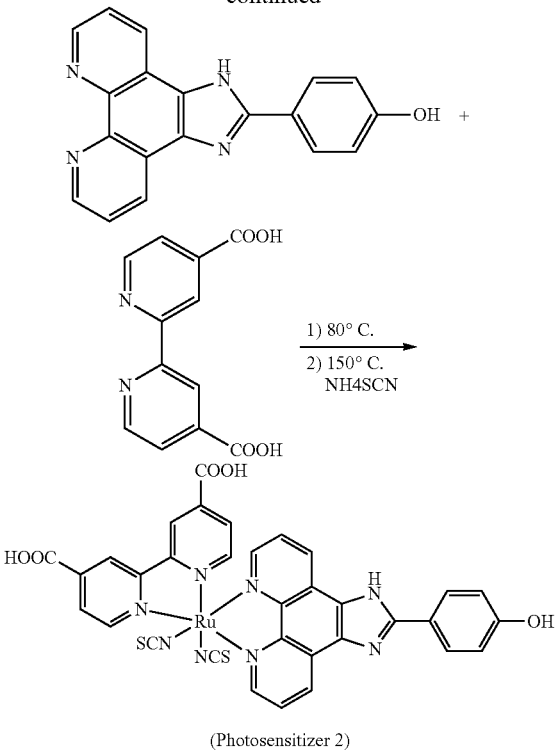

(Photosensitizer 2)

Example 3

Synthesis of Compound 3

Dipyridylamine (5.84 mmol; 1 g), 4-bromoanisole (8.76 mmol; 1.64 g), potassium hydroxide (8.75 mmol; 0.5 g) and copper sulfate (0.18 mmol; 30 mg) as a catalyst were mixed and stirred while being heated at a temperature of 180° C. for 6 hours. After completion of the reaction, the mixture was allowed to cool and chloroform and water were added thereto. After the mixture was washed with water, the solvent was vacuum-distilled on magnesium sulfate thereby obtaining an intended product. The intended product was dissolved in chloroform and refined with a column MeOH/CHCl$_3$ (1/10) thereby producing Compound 3 at a yield of 65%. Compound 3 was identified with NMR.

Synthesis of Photosensitizer 3

Dichloro(p-cymen)ruthenium dimmer ([RuCl$_2$(p-cymene)]$_2$) (1 mmol; 0.61 g) and Compound 3 (2 mmol; 0.65 g) were dissolved in dimethylformamide (50 ml), and then stirred at a temperature of 80° C. under an argon atmosphere for 2 hours. Thereafter, 2,2'-bipyridine-4,4'-carboxylic acid (2 mmol) was added to the mixture and stirred while being heated at a temperature of 150° C. under an argon atmosphere for 5 hours. Further, ammonium thiocyanate (1.5 g) was added to the mixture and stirred while being heated for 4 hours.

Figure 3:
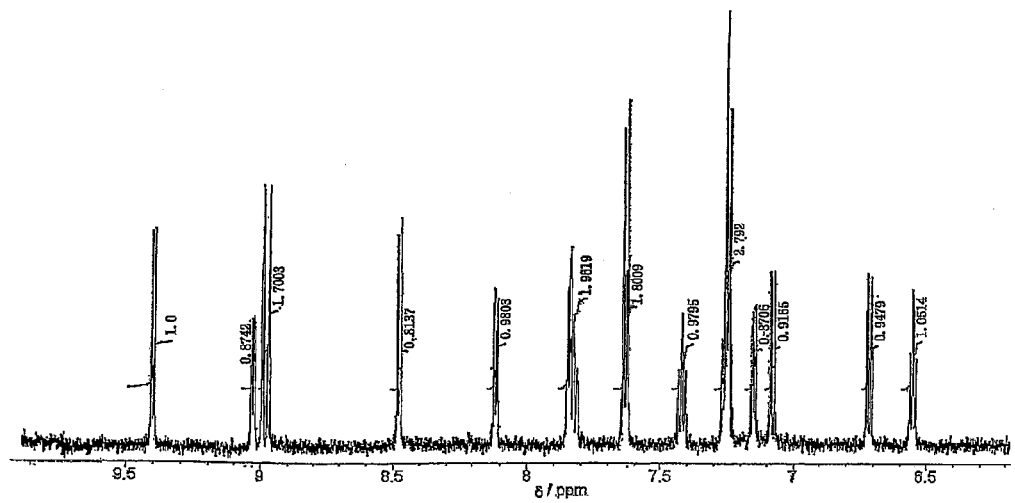
FIG. 3 is an $^1$H-NMR spectrum of Photosensitizer 3.
Figure 3:
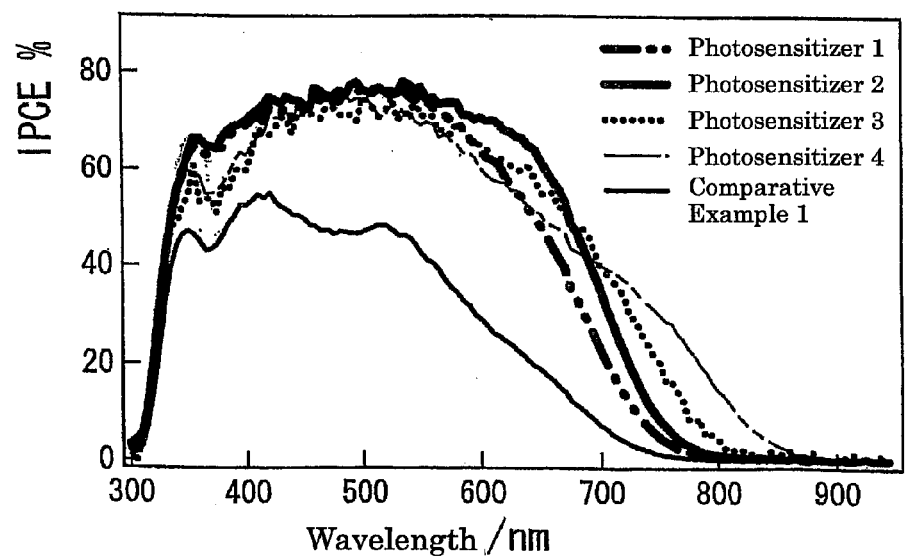

After completion of the reaction, the mixture was vacuum-concentrated and the resulting residue was dispersed in water and filtered thereby producing an intended product in the form of a crude refined product. An aqueous solution of n-butylammonium hydroxide was added in methanol and the intended product was dissolved therein, and then refined with a column (Sephadex LH-20). After the main component thus obtained was vacuum-concentrated, it was diluted with water and made at a pH of 2 with an aqueous solution of diluted HNO₃. The resulting deep red deposit was recovered by filtration and then vacuum-dried thereby producing intended Photosensitizer 3 at a yield of 70 percent. Photosensitizer 3 was identified with MS spectrum and ¹H-NMR spectrum. FIG. 3 shows the ¹H-NMR spectrum of Photosensitizer 3.

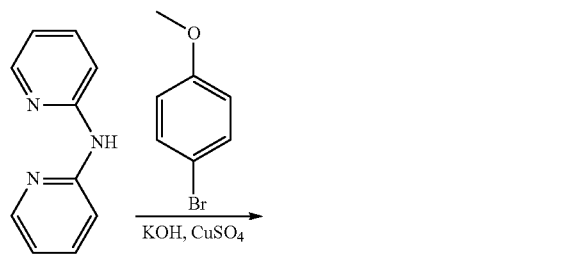

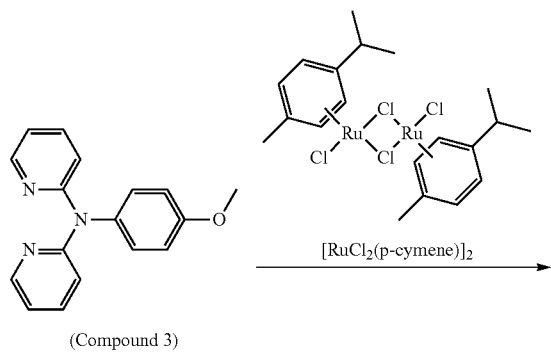

(Compound 3)

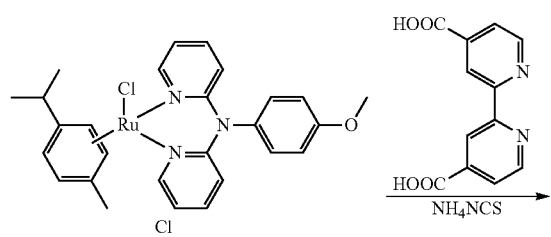

-continued

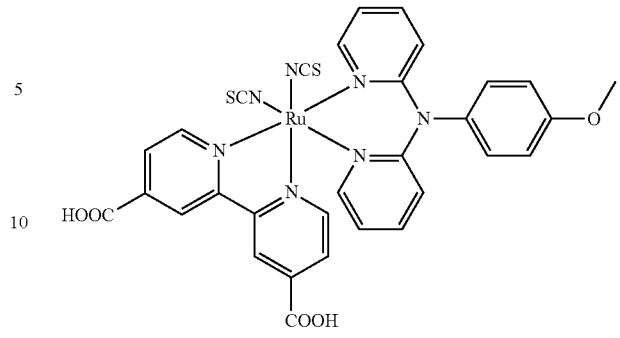

(Photosensitizer 3)

Example 4

Synthesis of Photosensitizer 4

Dichloro(p-cymen)ruthenium dimmer ([RuCl₂(p-cymene)]₂) (1 mmol; 0.61 g) and Compound 3 (2 mmol; 0.65 g) were dissolved in dimethylformamide (50 ml), and then stirred at a temperature of 80° C. under an argon atmosphere for 2 hours. Thereafter, 4,4'-bis(carboxvinyl)-2,2'-bipyridine (2 mmol) was added to the mixture and stirred while being heated at a temperature of 150° C. under an argon atmosphere for 5 hours. Further, ammonium thiocyanate (1.5 g) was added to the mixture and stirred while being heated for 4 hours.

After completion of the reaction, the mixture was vacuum-concentrated and the resulting residue was dispersed in water and filtered thereby producing an intended product in the form of a crude refined product. An aqueous solution of n-butylammonium hydroxide was added in methanol and the intended product was dissolved therein, and then refined with a column (Sephadex LH-20). After the main component thus obtained was vacuum-concentrated, it was diluted with water and made at a pH of 2 with an aqueous solution of diluted HNO₃. The resulting deep red deposit was recovered by filtration and then vacuum-dried thereby producing intended Photosensitizer 4 at a yield of 70 percent. Photosensitizer 4 was identified with MS spectrum and ¹H-NMR spectrum.

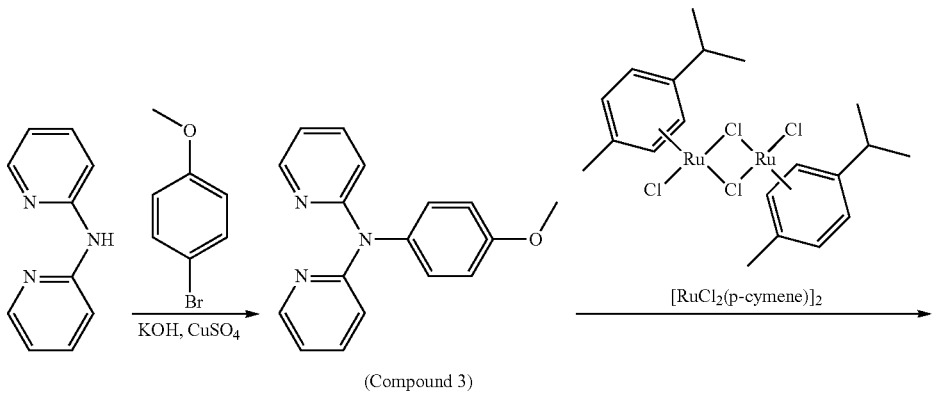

(Compound 3)

-continued

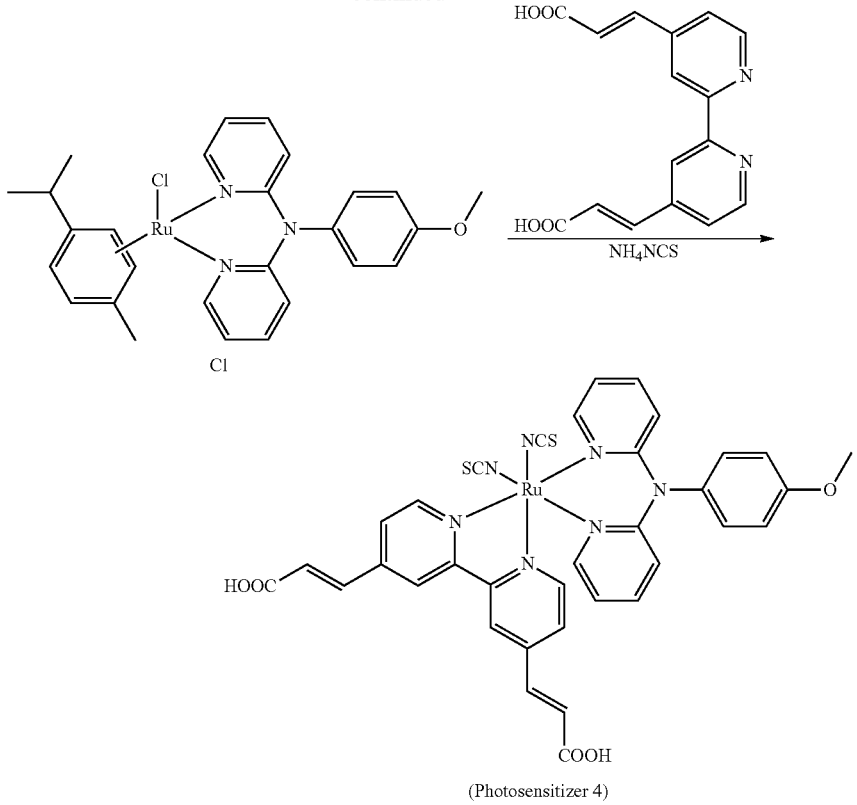

(Photosensitizer 4)

Preparation of Photovoltaic Cell and Measurement of Conversion Efficiency

A photovoltaic cell utilizing the sensitization of a titanium oxide film supported on an electrically conductive substrate was prepared as follows.

Colloidal $TiO_2$ particles (particle diameter: 20 to 30 nm) were coated over an electrically conductive glass (fluorine-doped $SnO_2$, 10Ω) and calcined at a temperature of 450° C. for 30 minutes (film thickness: 10 μm). In order to scatter light, $TiO_2$ particles (particle diameter: 300 to 400 nm) were coated over the resulting film and calcined at a temperature of 520° C. for one hour (film thickness: 6 to 8 μm). This two-layered film was immersed in a $TiCl_4$ solution for 30 minutes and then heated at a temperature of 450° C. for 30 minutes.

The resulting film was immersed in a solution of each of the above-produced photosensitizers and ethanol ($3.0 \times 10^{-4}$ mol/L) for 15 hours thereby producing a dye layer. The resulting substrate was brought into contact with a glass substrate with a Pt film so that the Pt film faces the dye layer, and then an acetonitrile solution containing 0.3 mol/L of lithium iodide and 0.03 mol/L of iodine was allowed to permeate therebetween utilizing capillary phenomenon. Thereafter, the periphery between the substrates was sealed with an epoxy adhesive. Lead wires were connected to the electrically conductive layer portions of the transparent electrically conductive substrate and the counter electrode.

The cell thus produced was irradiated with an artificial sunlight to measure the photovoltaic conversion characteristics. The results of measurement of the short circuit current (Jsc) and incident photon-to-current conversion efficiency (IPCE) are shown in Table 1 and FIG. 4, respectively.

Comparative Example 1

In order to prove the effect obtained by ΔL>0.25 eV, a solar battery cell was produced using Photosensitizer 5 with a ΔL of less than 0.25 eV with the same procedures of Examples 1 to 4.

As apparent from Table 1 below, Photosensitizers 1 to 4 according to the present invention are larger in short circuit current and more excellent in current conversion efficiency of incident photon in a region of 780 nm, than Photosensitizer 5 with a less ΔL. The ΔL needs to be at least 0.25 eV or more in order to obtain a higher conversion efficiency.

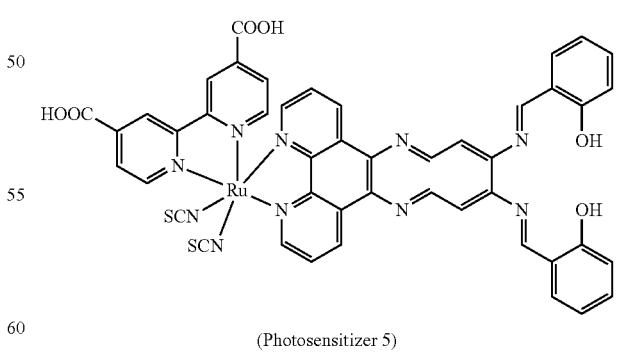

(Photosensitizer 5)

It is confirmed from Table 1 that Photosensitizers 1 to 4 according to the present invention are larger in short circuit current than Photosensitizer 5 of Comparative Example 1. It is also confirmed from FIG. 4 that the photosensitizers of the present invention are superior in the current conversion efficiencies in the range of 400 to 700 nm and a region of 780 nm to Photosensitizer 5 of Comparative Example 1.

TABLE 1

| Experiments | Dye | Shortcircuit Current Jsc mA/cm$^2$ | IPCE (@780 nm) % | ΔL eV |
|---|---|---|---|---|
| Example 1 | Photosensitizer 1 | 15.4 | 3 | 0.48 |
| Example 2 | Photosensitizer 2 | 16.6 | 5 | 0.48 |
| Example 3 | Photosensitizer 3 | 17.9 | 15 | 0.61 |
| Example 4 | Photosensitizer 4 | 16 | 30 | 1.3 |
| Comparative Example 1 | Photosensitizer 5 | 9 | 1 | 0.23 |

APPLICABILITY IN THE INDUSTRY

The novel photosensitizer of the present invention can absorb light in a wide visible region so as to increase the conversion efficiency of a photovoltaic device and thus is significantly useful in the industry.

The invention claimed is:

1. A photosensitizer for metal oxide semiconductor electrodes, comprising a metal complex represented by formula (I) below, wherein when the photosensitizer is adsorbed on a metal oxide semiconductor electrode via ligands $L^1$ and $L^2$, the difference ΔL between the energy levels of ligands $L^1$ and $L^2$ in their excited states, calculated in accordance with a GAUSSIAN03 quantum chemistry calculation program is 0.25 eV or more:

$$ML^1L^2X_2 \quad (I)$$

wherein M is a group 8 transition metal of the periodic table, Xs are each independently a halogen atom, a cyano group, a thiocyanate group, an isothiocyanate group, an isocyanate group, an isocyanide group or a hydroxyl group, or a bidentate ligand represented by formula (A) below in the case where Xs are bonded to one another, $L^1$ and $L^2$ are each a ligand having an aromatic ring, and either $L^1$ or $L^2$ has a functional group having a COOH group or PO(OH)$_2$ or a functional group to which a COOH group or PO(OH)$_2$ is bonded via π conjugation:

(A)

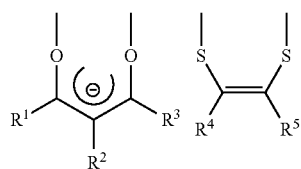

wherein $R^1$ through $R^3$ are the same as or different from each other and are each independently hydrogen, an alkyl group having 1 to 30 carbon atoms, an alkoxyalkyl group having 2 to 30 carbon atoms, a perfluoroalkyl group having 1 to 30 carbon atoms, an aryl group having 6 to 30 carbon atoms, or an aralkyl group having 7 to 30 carbon atoms, and $R^4$ and $R^5$ are each independently hydrogen, a cyano group, an alkyl group having 1 to 20 carbon atoms, a perfluoroalkyl group having 1 to 20 carbon atoms, or an aryl group having 6 to 15 carbon atoms and may be bonded to one another to form a ring, and wherein in formula (I), $L^1$ is a ligand represented by formula (II) below and $L^2$ is a ligand represented by formula (III) below:

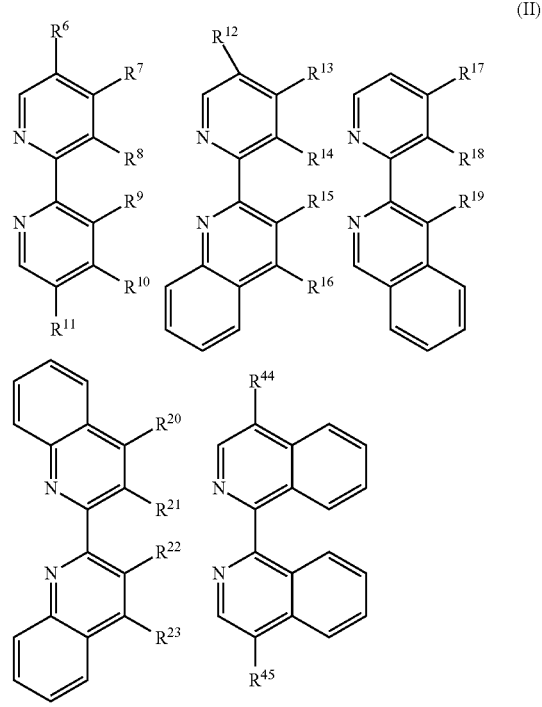

(II)

wherein $R^6$ through $R^{11}$, $R^{12}$ through $R^{16}$, $R^{17}$ through $R^{19}$, $R^{20}$ through $R^{23}$, and $R^{44}$ through $R^{45}$ are the same as or different from each other and are each independently a functional group having a COOH group or PO(OH)$_2$, a functional group to which a COOH group or PO(OH)$_2$ is bonded via π conjugation, hydrogen, an alkyl group having 1 to 30 carbon atoms, an alkenyl group, an aryl group, an alkoxy group, or an amino group;

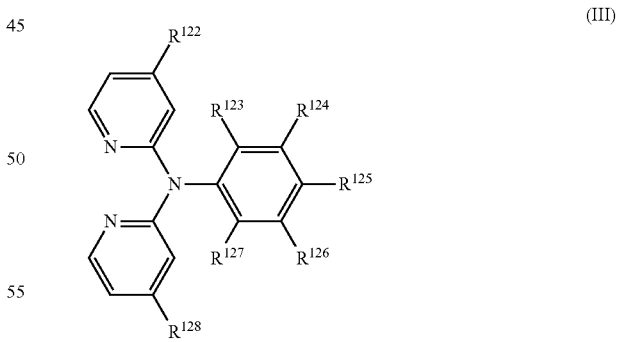

(III)

wherein $R^{122}$ through $R^{128}$ are each independently a functional group having a COOH group or PO(OH)$_2$, a functional group to which a COOH group or PO(OH)$_2$ is bonded via π conjugation, hydrogen, an OH group, a methoxy group, halogen, an alkyl group having 1 to 30 carbon atoms, an alkoxy group, an amino group, a cyano group, or a nitro group.

2. The photosensitizer according to claim 1 wherein in formula (I) $L^1$ contains a functional group having at least one COOH group or PO(OH)$_2$ or a functional group to which a COOH group or PO(OH)$_2$ is bonded via π conjugation, L$^2$ does not contain a COOH group or PO(OH)$_2$, and when the photosensitizer is adsorbed on a metal oxide semiconductor electrode via L$^1$, the energy level of L$^2$ in its excited state is higher than that of L$^1$ by at least 0.25 eV or more.

3. A photovoltaic device having at least one metal oxide semiconductor layer, wherein the metal oxide semiconductor layer comprises the photosensitizer according to claim 1.

4. A photovoltaic device having at least one metal oxide semiconductor layer, wherein the metal oxide semiconductor layer comprises the photosensitizer according to claim 2.

* * * * *